US011058354B2

(12) United States Patent
Mahapatra et al.

(10) Patent No.: US 11,058,354 B2
(45) Date of Patent: *Jul. 13, 2021

(54) ACCESS NEEDLE WITH DIRECT VISUALIZATION AND RELATED METHODS

(71) Applicant: University of Virginia Patent Foundation, Charlottesville, VA (US)

(72) Inventors: Srijoy Mahapatra, Charlottesville, VA (US); George T. Gillies, Charlottesville, VA (US); Jason M. Tucker-Schwartz, Nashville, TN (US)

(73) Assignee: University of Virginia Patent Foundation, Charlottesville, VA (US)

( * ) Notice: Subject to any disclaimer, the term of this patent is extended or adjusted under 35 U.S.C. 154(b) by 848 days.

This patent is subject to a terminal disclaimer.

(21) Appl. No.: 14/879,849

(22) Filed: Oct. 9, 2015

(65) Prior Publication Data

US 2016/0100797 A1 Apr. 14, 2016

Related U.S. Application Data

(63) Continuation-in-part of application No. 13/464,762, filed on May 4, 2012, now Pat. No. 9,468,396, which
(Continued)

(51) Int. Cl.
*A61B 5/00* (2006.01)
*A61B 17/34* (2006.01)
(Continued)

(52) U.S. Cl.
CPC .......... *A61B 5/4887* (2013.01); *A61B 5/0044* (2013.01); *A61B 5/03* (2013.01);
(Continued)

(58) Field of Classification Search
CPC ... A61B 5/0044; A61B 5/4887; A61B 5/6848; A61B 17/3403; A61B 5/03; A61B 5/7257; A61B 5/7203; A61B 5/065
See application file for complete search history.

(56) References Cited

U.S. PATENT DOCUMENTS 3,794,026 A 2/1974 Jacobs
4,349,023 A 9/1982 Gross
(Continued)

FOREIGN PATENT DOCUMENTS

AU 70522/96 1/1997
CA 2236958 5/1998
(Continued)

OTHER PUBLICATIONS

Aliot et al., "EHRA/HRS expert consensus on catheter albation of ventricular arrhythmias," Europace, vol. 11, No. 6, pp. 771-817, 2009.
(Continued)

*Primary Examiner* — Theodore J Stigell
(74) *Attorney, Agent, or Firm* — Jenkins, Wilson, Taylor & Hunt, P.A.; Robert J. Decker

(57) ABSTRACT

Systems and methods for epicardial electrophysiology and other procedures are provided in which the location of an access needle may be inferred according to the detection of different pressure frequencies in separate organs, or different locations, in the body of a subject. Methods may include inserting a needle including a first sensor into a body of a subject, and receiving pressure frequency information from the first sensor. A second sensor may be included with the access needle to provide image data and/or cardiac waveform information of the subject.

26 Claims, 17 Drawing Sheets

Related U.S. Application Data is a continuation-in-part of application No. 12/530,830, filed as application No. PCT/US2008/056643 on Mar. 12, 2008, now Pat. No. 8,282,565, and a continuation of application No. PCT/US2011/025470, filed on Feb. 18, 2011.

(60) Provisional application No. 62/062,010, filed on Oct. 9, 2014, provisional application No. 62/237,818, filed on Oct. 6, 2015, provisional application No. 61/482,527, filed on May 4, 2011, provisional application No. 60/918,782, filed on Mar. 19, 2007, provisional application No. 61/305,560, filed on Feb. 18, 2010, provisional application No. 61/442,836, filed on Feb. 15, 2011.

(51) Int. Cl.
*A61B 5/03* (2006.01)
*A61B 5/0205* (2006.01)
*A61B 5/06* (2006.01)
*A61B 5/0215* (2006.01)
*A61B 5/0402* (2006.01)
*A61B 5/318* (2021.01)

(52) U.S. Cl.
CPC .......... *A61B 5/6848* (2013.01); *A61B 5/7257* (2013.01); *A61B 17/3403* (2013.01); *A61B 5/0084* (2013.01); *A61B 5/0215* (2013.01); *A61B 5/02055* (2013.01); *A61B 5/065* (2013.01); *A61B 5/318* (2021.01); *A61B 5/7203* (2013.01)

(56) References Cited

U.S. PATENT DOCUMENTS

| | | |
|---|---|---|
| 4,607,644 A | 8/1986 | Pohndorf |
| 4,817,634 A | 4/1989 | Holleman |
| 4,971,070 A | 11/1990 | Holleman |
| 4,991,603 A | 2/1991 | Cohen |
| 5,033,477 A | 7/1991 | Chin |
| 5,071,428 A | 12/1991 | Chin |
| 5,213,570 A | 5/1993 | VanDeripe |
| 5,269,326 A | 12/1993 | Verrier |
| 5,300,110 A | 4/1994 | Latterell |
| 5,335,313 A | 8/1994 | Douglas |
| 5,336,252 A | 8/1994 | Cohen |
| 5,395,349 A | 3/1995 | Quiachon |
| 5,465,711 A | 11/1995 | Moll |
| 5,484,423 A | 1/1996 | Waskonig |
| 5,509,924 A | 4/1996 | Paspa |
| 5,544,654 A | 8/1996 | Murphy |
| 5,669,882 A | 9/1997 | Pyles |
| 5,679,005 A | 10/1997 | Einstein |
| 5,702,438 A | 12/1997 | Avitall |
| 5,725,504 A | 3/1998 | Collins |
| 5,733,280 A | 3/1998 | Avitall |
| 5,779,699 A | 7/1998 | Lipson |
| 5,797,870 A | 8/1998 | March |
| 5,800,428 A | 9/1998 | Nelson |
| 5,812,978 A | 9/1998 | Nolan |
| 5,827,216 A | 10/1998 | Igo |
| 5,843,048 A | 12/1998 | Gross |
| 5,846,239 A | 12/1998 | Swanson |
| 5,885,217 A | 3/1999 | Gisselberg |
| 5,916,194 A | 6/1999 | Jacobsen |
| 5,931,810 A | 8/1999 | Grabek |
| 5,970,457 A | 10/1999 | Brant |
| 5,972,013 A | 10/1999 | Schmidt |
| 6,036,685 A | 3/2000 | Mueller |
| 6,051,008 A | 4/2000 | Saadat |
| 6,123,084 A | 9/2000 | Jandak |
| 6,148,825 A | 11/2000 | Anderson |
| 6,156,009 A | 12/2000 | Grabek |
| 6,156,018 A | 12/2000 | Hassett |
| 6,162,195 A | 12/2000 | Igo |
| 6,200,303 B1 | 3/2001 | Verrior |
| 6,206,004 B1 | 3/2001 | Schmidt |
| 6,231,518 B1 | 5/2001 | Grabek |
| 6,234,804 B1 | 5/2001 | Yong |
| 6,237,605 B1 | 5/2001 | Vaska |
| 6,263,241 B1 | 7/2001 | Rosborough |
| 6,266,567 B1 | 7/2001 | Ishikawa |
| 6,270,476 B1 | 8/2001 | Santoianni |
| 6,270,484 B1 | 8/2001 | Yoon |
| 6,273,877 B1 | 8/2001 | West |
| 6,278,975 B1 | 8/2001 | Brant |
| 6,314,963 B1 | 11/2001 | Vaska |
| 6,322,536 B1 | 11/2001 | Rosengart |
| 6,325,776 B1 | 12/2001 | Anderson |
| 6,416,505 B1 | 7/2002 | Fleischman |
| 6,423,051 B1 | 7/2002 | Kaplan |
| 6,500,130 B2 | 12/2002 | Kinsella |
| 6,527,767 B2 | 3/2003 | Wang |
| 6,551,289 B1 | 4/2003 | Higuchi |
| 6,554,809 B2 | 4/2003 | Aves |
| 6,558,382 B2 | 5/2003 | Jahns |
| 6,569,082 B1 | 5/2003 | Chin |
| 6,592,552 B1 | 7/2003 | Schmidt |
| 6,613,062 B1 | 9/2003 | Lechrone |
| 6,616,676 B2 | 9/2003 | Bashiri |
| 6,666,844 B1 | 12/2003 | Igo |
| 6,666,861 B1 | 12/2003 | Grabek |
| 6,689,128 B2 | 2/2004 | Sliwa |
| 6,711,436 B1 | 3/2004 | Duhaylongsod |
| 6,723,092 B2 | 4/2004 | Brown |
| 6,752,805 B2 | 6/2004 | Maguire |
| 6,771,996 B2 | 8/2004 | Bowe |
| 6,783,510 B1 | 8/2004 | Gibson |
| 6,786,898 B2 | 9/2004 | Guenst |
| 6,811,544 B2 | 11/2004 | Schaer |
| 6,827,714 B2 | 12/2004 | Swanson |
| 6,827,715 B2 | 12/2004 | Francischelli |
| 6,835,193 B2 | 12/2004 | Epstein |
| 6,837,848 B2 | 1/2005 | Bonner |
| 6,837,886 B2 | 1/2005 | Collins |
| 6,849,075 B2 | 2/2005 | Bertolero |
| 6,868,291 B1 | 3/2005 | Bonner |
| 6,869,414 B2 | 3/2005 | Simpson |
| 6,876,885 B2 | 4/2005 | Swoyer |
| 6,899,710 B2 | 5/2005 | Hooven |
| 6,916,318 B2 | 7/2005 | Francischelli |
| 6,918,890 B2 | 7/2005 | Schmidt |
| 6,918,908 B2 | 7/2005 | Bonner |
| 6,921,295 B2 | 7/2005 | Sommer |
| 6,928,313 B2 | 8/2005 | Peterson |
| 6,936,040 B2 | 8/2005 | Kramm |
| 6,960,205 B2 | 11/2005 | Jahns |
| 6,968,223 B2 | 11/2005 | Hanover |
| 6,973,352 B1 | 12/2005 | Tsutsui |
| 6,974,454 B2 | 12/2005 | Hooven |
| 7,004,937 B2 | 2/2006 | Lentz |
| 7,008,418 B2 | 3/2006 | Hall |
| 7,027,876 B2 | 4/2006 | Casavant |
| 7,037,296 B2 | 5/2006 | Kadziauskas |
| 7,041,099 B2 | 5/2006 | Thomas |
| 7,059,878 B1 | 6/2006 | Hendrixson |
| 7,063,693 B2 | 6/2006 | Guenst |
| 7,085,606 B2 | 8/2006 | Flach |
| 7,089,063 B2 | 8/2006 | Lesh |
| 7,090,637 B2 | 8/2006 | Danitz |
| 7,101,362 B2 | 9/2006 | Vanney |
| 7,104,986 B2 | 9/2006 | Hovda |
| 7,120,504 B2 | 10/2006 | Osypka |
| 7,130,699 B2 | 10/2006 | Huff |
| 7,142,919 B2 | 11/2006 | Hine |
| 7,146,225 B2 | 12/2006 | Guenst |
| 7,147,633 B2 | 12/2006 | Chee |
| 7,207,988 B2 | 4/2007 | Leckrone |
| 7,214,180 B2 | 5/2007 | Chin |
| 7,226,448 B2 | 6/2007 | Bertolero |
| 7,226,458 B2 | 6/2007 | Kaplan |

(56) References Cited

U.S. PATENT DOCUMENTS

| | | | |
|---|---|---|---|
| 7,232,422 B2 | 6/2007 | Gibson | |
| 7,247,139 B2 | 7/2007 | Yudkovitch | |
| 7,259,906 B1 | 8/2007 | Islam | |
| 7,264,587 B2 | 9/2007 | Chin | |
| 7,286,992 B2 | 10/2007 | Sander | |
| 7,309,328 B2 | 12/2007 | Kaplan | |
| 7,398,781 B1 | 7/2008 | Chin | |
| 7,468,029 B1 | 12/2008 | Robertson | |
| 7,473,244 B2 | 1/2009 | Frazier | |
| 8,282,565 B2* | 10/2012 | Mahapatra | A61B 5/4887 600/486 |
| 9,218,752 B2 | 12/2015 | Gillies et al. | |
| 9,314,265 B2* | 4/2016 | Mahapatra | A61B 5/4887 |
| 9,468,396 B2* | 10/2016 | Mahapatra | A61B 5/03 |
| 9,642,534 B2* | 5/2017 | Mahapatra | A61B 5/061 |
| 2001/0020166 A1 | 9/2001 | Daly | |
| 2001/0039410 A1 | 11/2001 | Verrier | |
| 2002/0045895 A1 | 4/2002 | Sliwa | |
| 2002/0055714 A1 | 5/2002 | Rothschild | |
| 2002/0058925 A1 | 5/2002 | Kaplan | |
| 2002/0072737 A1 | 6/2002 | Belden | |
| 2002/0082523 A1 | 6/2002 | Kinsella | |
| 2002/0161361 A1 | 10/2002 | Sherman | |
| 2003/0028187 A1 | 2/2003 | Vaska | |
| 2003/0065318 A1 | 4/2003 | Pendekanti | |
| 2003/0069572 A1 | 4/2003 | Wellman | |
| 2003/0114796 A1 | 6/2003 | Schmidt | |
| 2003/0181855 A1 | 9/2003 | Simpson | |
| 2004/0024397 A1 | 2/2004 | Griffin | |
| 2004/0024413 A1 | 2/2004 | Lentz | |
| 2004/0024435 A1 | 2/2004 | Leckrone | |
| 2004/0034365 A1 | 2/2004 | Lentz | |
| 2004/0064138 A1 | 4/2004 | Grabek | |
| 2004/0087831 A1 | 5/2004 | Michels | |
| 2004/0087938 A1 | 5/2004 | Leckrone | |
| 2004/0102804 A1 | 5/2004 | Chin | |
| 2004/0126746 A1 | 7/2004 | Toly | |
| 2004/0138526 A1 | 7/2004 | Guenst | |
| 2004/0138527 A1 | 7/2004 | Bonner | |
| 2004/0138531 A1 | 7/2004 | Bonner | |
| 2004/0147826 A1 | 7/2004 | Peterson | |
| 2004/0176679 A1 | 9/2004 | Murphy et al. | |
| 2004/0186507 A1 | 9/2004 | Hall | |
| 2004/0215168 A1 | 10/2004 | Verrier | |
| 2004/0216748 A1 | 11/2004 | Chin | |
| 2004/0267303 A1 | 12/2004 | Guenst | |
| 2004/0267326 A1 | 12/2004 | Ocel | |
| 2005/0004514 A1 | 1/2005 | Hochman | |
| 2005/0020914 A1 | 1/2005 | Amundson | |
| 2005/0027243 A1 | 2/2005 | Gibson | |
| 2005/0085769 A1 | 4/2005 | MacMahon | |
| 2005/0154376 A1 | 7/2005 | Riviere | |
| 2005/0215945 A1 | 9/2005 | Harris et al. | |
| 2005/0234507 A1 | 10/2005 | Geske | |
| 2005/0251094 A1 | 11/2005 | Peterson | |
| 2005/0256368 A1 | 11/2005 | Klenk | |
| 2005/0261673 A1 | 11/2005 | Bonner | |
| 2005/0273006 A1 | 12/2005 | Stewart | |
| 2005/0273144 A1 | 12/2005 | Lennox | |
| 2006/0025705 A1 | 2/2006 | Whittaker | |
| 2006/0025762 A1 | 2/2006 | Mohan | |
| 2006/0041243 A1 | 2/2006 | Nayak | |
| 2006/0052660 A1 | 3/2006 | Chin | |
| 2006/0064056 A1 | 3/2006 | Coyle | |
| 2006/0064058 A1 | 3/2006 | Coyle | |
| 2006/0074397 A1 | 4/2006 | Shimada | |
| 2006/0106442 A1 | 5/2006 | Richardson | |
| 2006/0122591 A1 | 6/2006 | Keidar | |
| 2006/0189840 A1 | 8/2006 | Walsh | |
| 2006/0200002 A1 | 9/2006 | Guenst | |
| 2006/0229490 A1 | 10/2006 | Chin | |
| 2006/0247522 A1 | 11/2006 | McGee | |
| 2006/0247672 A1 | 11/2006 | Vidlund | |
| 2006/0259017 A1 | 11/2006 | Heil | |
| 2006/0270900 A1 | 11/2006 | Chin | |
| 2006/0271032 A1 | 11/2006 | Chin | |
| 2007/0016068 A1 | 1/2007 | Grunwald | |
| 2007/0016069 A1 | 1/2007 | Grunwald | |
| 2007/0016070 A1 | 1/2007 | Grunwald | |
| 2007/0016072 A1 | 1/2007 | Grunwald | |
| 2007/0032796 A1 | 2/2007 | Chin-Chen | |
| 2007/0038052 A1 | 2/2007 | Swoyer | |
| 2007/0043397 A1 | 2/2007 | Ocel | |
| 2007/0055142 A1 | 3/2007 | Webler | |
| 2007/0198041 A1 | 8/2007 | Rupp | |
| 2007/0270882 A1 | 11/2007 | Hjelle | |
| 2008/0015625 A1 | 1/2008 | Ventura | |
| 2008/0051671 A1 | 2/2008 | Broome | |
| 2008/0091109 A1 | 4/2008 | Abraham | |
| 2008/0097399 A1 | 4/2008 | Sachar | |
| 2008/0108945 A1 | 5/2008 | Kaplan | |
| 2008/0183080 A1 | 7/2008 | Abraham | |
| 2008/0208184 A1 | 8/2008 | Davies | |
| 2008/0262432 A1 | 10/2008 | Miller | |
| 2008/0294174 A1 | 11/2008 | Bardsley | |
| 2009/0068627 A1 | 3/2009 | Toly | |
| 2009/0069697 A1 | 3/2009 | Frazier | |
| 2009/0246747 A1 | 10/2009 | Buckman | |
| 2009/0253102 A1 | 10/2009 | Porikli et al. | |
| 2009/0311656 A1 | 12/2009 | Lundback et al. | |
| 2010/0094143 A1 | 4/2010 | Mahapatra | |
| 2010/0114093 A1 | 5/2010 | Mahapatra | |
| 2010/0211064 A1 | 8/2010 | Mahapatra | |
| 2010/0241185 A1 | 9/2010 | Mahapatra | |
| 2012/0249890 A1 | 10/2012 | Chardon et al. | |
| 2012/0274863 A1 | 11/2012 | Chardon et al. | |
| 2012/0278348 A1 | 11/2012 | Chardon et al. | |
| 2012/0310052 A1 | 12/2012 | Mahapatra | |
| 2012/0330184 A1 | 12/2012 | Mahapatra | |
| 2013/0108999 A1 | 5/2013 | Gillies | |
| 2015/0297073 A1* | 10/2015 | Nguyen | A61B 1/317 600/103 |

FOREIGN PATENT DOCUMENTS

| | | |
|---|---|---|
| DE | 43 13 903 C1 | 9/1994 |
| EP | 0 450 608 A1 | 10/1991 |
| EP | 1129681 | 9/2001 |
| EP | 1 181 896 | 2/2002 |
| WO | WO 87/04081 | 7/1987 |
| WO | WO 93/20878 | 10/1993 |
| WO | WO 93/20886 | 10/1993 |
| WO | WO 95/10319 | 4/1995 |
| WO | WO 95/15115 | 6/1995 |
| WO | WO 97/33526 | 9/1997 |
| WO | WO 99/18869 | 4/1999 |
| WO | WO 01/05306 | 1/2001 |
| WO | WO 01/58373 | 8/2001 |
| WO | WO 01/68173 | 9/2001 |
| WO | WO 01/80724 | 11/2001 |
| WO | WO 01/80757 | 11/2001 |
| WO | WO 01/93930 | 12/2001 |
| WO | WO 2008/112870 | 9/2008 |
| WO | WO 2008/115745 | 9/2008 |
| WO | WO 2008/118737 | 10/2008 |
| WO | WO 2009/062061 | 5/2009 |
| WO | WO 2011/103456 | 8/2011 |

OTHER PUBLICATIONS

Arrow International Corporation, AN-05505 Epidural Needle, www.arrowintl.com/products/boms/AN05505.asp?cat=17&item=AN-05505&xsec=(accessed Feb. 13, 2007).

Beukema, "Radiofrequency Ablation of Atrial Fibrillation in Patients Undergoing Concommitant Cardiac Surgery. First Experience," PACE, 1997, p. 1100, vol. 20, (Part II).

D'Avila "Transthoracic Epicardial Catheter Ablation of Ventricular Tachycardia," Heart Rhythm, 2006, p. 1110-1111, vol. 3.

Derose, Jr., "Robotically Assisted Left Ventricular Epicardial Lead Implantation for Biventricular Pacing: the Posterior Approach," The Annals of Thoracic Surgery, 2004, p. 1472-1474, vol. 77.

(56) References Cited

OTHER PUBLICATIONS

DP25B-S Strainn Gage Pagel Meter: User's Guide OMEGA Engineering, Inc., 2002 (accessed Jul. 9, 2007), Stamford, CT. Online at http://www.omega.com/Manuals/manualpdf/M3598.pdf.

DP41B Universal Input Meter: User's Guide, OMEGA Engineering, Inc., 1996 (accessed Dec. 5, 2007). Stamford, CT. Online at http://www.omega.comManuals/manualpdf.M2544.pdf.

DPI 603 Portable Pressure Calibrator User Guide, OMEGA Engineering, Inc., 1996 (accessed Dec. 5, 2007), Stamford, CT. Online at http://www.omega.com/Manual.pdf/M2913.pdf.

E. Sosa and M. Scanavacca, "Epicardial mapping and ablation techniques to control ventricular tachycardia," J. Cardiovasc. Electrophysiol., vol. 16, No. 4, pp. 449-52, 2005.

E. Sosa et al., "A new technique to perform epicardial mapping in the electrophysiology laboratory," J. Cardiovasc. Electrophysiol., vol. 7, No. 6, pp. 531-536, 1996.

Frolich, "Pioneers in Epidural Needle Design," Anesthesia & Analgesia, 2001, p. 215-220, vol. 93.

Grimard et al., "Precutaneous epicardial radiofrequency albation of ventricular arrhythmias after failure of endocardial epproach: a 9-year experience," J. Cardiovasc. Electrophysiol., vol. 21, No. 1, pp. 56-61, 2010.

Hansky, "Lead Selection and Implantation Technique for Biventricular Pacing," European Heart Journal Supplements, 2004, p. D112-D116, vol. 6, Supplement D.

J. Tucker-Schwartz et al., "Improved Pressure-Frequency Sensing Subxiphoid Pericardial Access System: Performance Characteristics During In Vivo testing," IEEE Transaction on Biomedical Engineering, vol. 58, pp. 845-852 (Apr. 2011).

J. Tucker-Schwartz, "Pressure frequency characteristics of the percardial space and thorax during subxiphoid access for epicardial ventricular tachycardia ablation," Heart Rhythm, vol. 7, No. 5, pp. 604-609, 2010.

Klein, "Radiofrequency Ablation of Cardiac Arrhythmias," Scientific American Science & Medicine 1994, p. 48-57.

Lin, "Catheter Microwave Ablation Therapy for Cardiac Arrhythmias," Bioelectromagnetics, 1999, p. 120-132, vol. 20.

Mahapatra, "Access Device and Manometric Monitoring System for Epicardial Electrophysiology: Improved Prototype and Use in Human Trials," Jul. 2007, Technical Report No. UVA/640419/MAE08/101.

Mahapatra, "Access Device and Manometric Monitoring System for Epicardial Electrophysiology: Improved Prototype and Use in Human Trials," Jan. 2008, Technical Report No. UVA/640419/MAE08/102.

Mahapatra, "Incidence and Predictors of Cardiac Perforation after Permanent Pacemaker Placement," Heart Rhythm, 2005, p. 907-911, vol. 2, No. 9.

Mair, "Epicardial Lead Implantation Techniques for Bivenntricular Pacing via Left Lateral Mini-Thoracotomy, Video-Assisted Thoracoscopy, and Robotic Approach," The Heart Surgery Forum #2003-4883, 2003, p. 412-417, vol. 6 (5).

Moses, "Sirolimus-Eluting Stents Versus Standard Stents in Patients with Stenosis in a Native Coronary Artery," New England Journal of Medicine, 2003, p. 1315-1323, vol. 349, No. 14.

PX26 Series Pressurue Transducer: Instruction Sheet, OMEGA Engineering, Inc., 2004 (accessed Jul. 9, 2007), Stamford, CT. Online at http://www.omega.com/Pressure/pdf/PX26.pdf.

PX26 Series Pressure Transducer: Instruction Sheet, OMEGA Engineering, Inc., 2004 (accessed Dec. 5, 2007), Stamford, CT. Online at http:www.omega.com/Manualpdf/M1608.pdf.

Sarabanda, "Efficacy and Safety of Circumferential Pulmonary Vein Isolation Using a Novel Cryothermal Balloon Ablation System," Journal of the American College of Cardiology, 2005, p. 1902-1912, vol. 46, No. 10.

Sosa et al., "Endocardial and epicardial ablation guided by nonsurgical transthoracic epciardial mapping to treat recurrent ventricular tachycardia," J. Cardiovasc. Electrophysiol., vol. 9, No. 3, pp. 229-239, 1998.

Sosa et al., "Nonsurgical transthoracic epicardial catheter ablation to treat recurrent ventricular tachycardia occuring late after myocardial infarction," J. Am. Coll. Cardiol., vol. 35, No. 6, pp. 1442-1449, 2000.

Sosa, "Nonsurgical Transthoracic Epicardial Apporach in Patients with Ventricular Tachycardia and Previous Cardiac Surgery," Journal of Interventional Cardiac Electrophsiology, 2004, p. 281-288, vol. 10.

Stokes, U.S. Statutory Invention Registration H356, Nov. 3, 1987.

Thomas, "Analysis of Human Epidural Pressures," Regional Anesthesia, 1992, p. 212-215, vol. 17, No. 4.

Tomaske, "Do Daily Threshold Trend Fluctutations of Epicardial Leads Correlate with Pacing and Sensing Characteristics in Paediatric Patients," Europace, 2007, p. 662-668, vol. 9.

Tucker-Schwartz et al., "Pressure-Frequency Sensing Subxiphoid Access System for Use in Percutaneous Cardiac Electrophysiology: Prototype Design and Pilot Study Results," IEEE Transaction on Biomedical Engineering, vol. 56, pp. 1160-1168 (May 2009).

U. Tedrow and W. Stevenson, "Strategies for epicardial mapping and ablation of ventricular tachycardia," J. Cardiovasc. Electrophysiol., vol. 20, No. 6, pp. 710-713, 2009.

Notice of Allowance corresponding to U.S. Appl. No. 15/589,522 dated Mar. 24, 2021.

Intent to Grant corresponding to European Patent Application No. 08743794.3 dated Feb. 18, 2021.

\* cited by examiner

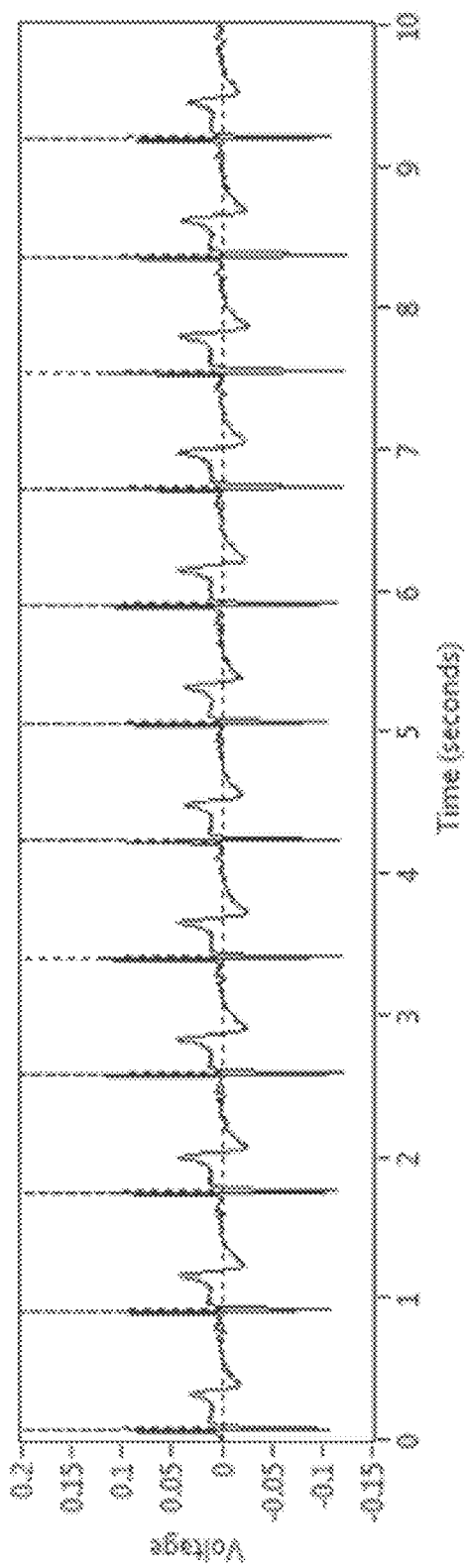
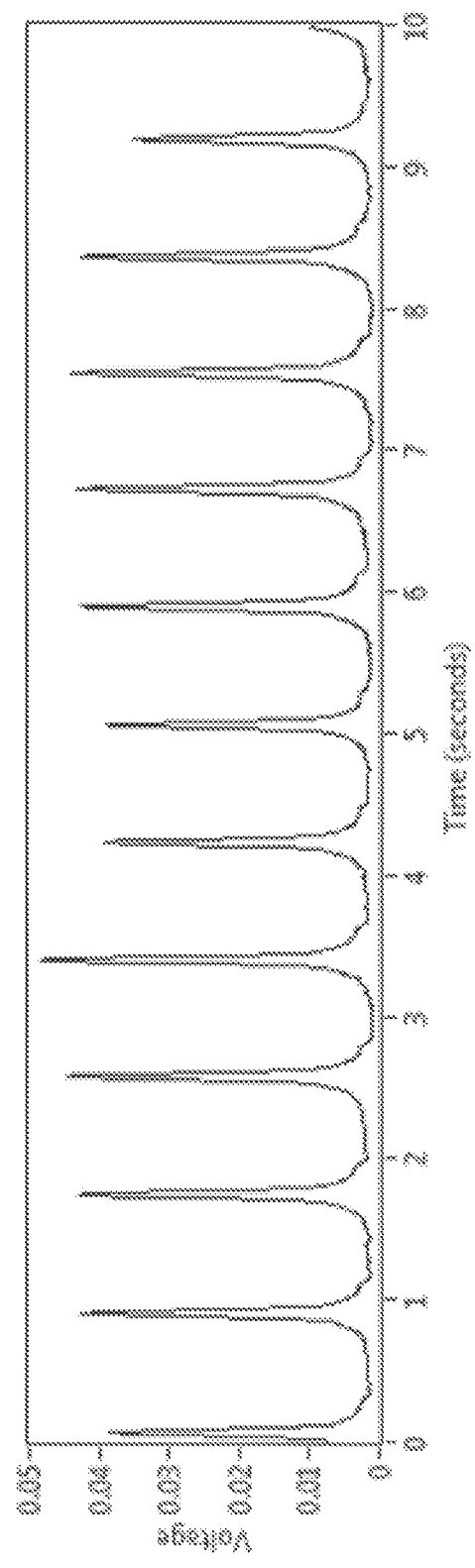
FIG. 2A
FIG. 2B

ACCESS NEEDLE WITH DIRECT VISUALIZATION AND RELATED METHODS

CROSS-REFERENCES TO RELATED APPLICATIONS

This application claims priority under 37 CFR § 1.78(a) to U.S. Provisional Application Ser. No. 62/062,010 filed on Oct. 9, 2014, and U.S. Provisional Application Ser. No. 62/237,818 filed on Oct. 6, 2015, and is a continuation in-part of U.S. patent application Ser. No. 13/464,762 filed on May 4, 2012, which claims priority under 37 CFR § 1.78(a) to U.S. Provisional Application Ser. No. 61/482,527 filed on May 4, 2011, and is a continuation in-part of U.S. patent application Ser. No. 12/530,830, filed Sep. 11, 2009, now U.S. Pat. No. 8,282,565 issued Oct. 9, 2012, which is a national stage entry of PCT/US2008/056643 filed Mar. 12, 2008, which claims priority under 37 CFR § 1.78(a) to U.S. Provisional Application Ser. No. 60/918,782 filed on Mar. 19, 2007, the contents of all of which are incorporated herein by reference in their entireties. U.S. application Ser. No. 13/464,762 is also a bypass continuation-in-part of PCT/US2011/025470 filed Feb. 18, 2011, and published as WO 2011/103456 on Aug. 25, 2011, which claims priority to U.S. Provisional Application Ser. No. 61/305,560 filed Feb. 18, 2010, and U.S. Provisional Application Ser. No. 61/442,836 filed Feb. 15, 2011, the contents of all of which are incorporated herein by reference in their entireties.

The present application is related to the following applications, of which all of the disclosures of the following applications are hereby incorporated by reference herein in their entireties:

U.S. patent application Ser. No. 13/607,993 entitled "Access Needle Pressure Sensor Device and Method of Use," filed Sep. 10, 2012; published as U.S. Patent Application Publication No. US-2012-0330184, Dec. 27, 2012;

PCT International Application Serial No. PCT/US2008/056643, filed Mar. 12, 2008, entitled, "Access Needle Pressure Sensor Device and Method of Use" and corresponding U.S. patent application Ser. No. 12/530,830 filed Sep. 11, 2009;

PCT International Application Serial No. PCT/US2008/056816, filed Mar. 13, 2008, entitled, "Epicardial Ablation Catheter and Method of Use" and corresponding U.S. patent application Ser. No. 12/530,938 filed Sep. 11, 2009;

PCT International Application Serial No. PCT/US2008/057626, filed Mar. 20, 2008, entitled, "Electrode Catheter for Ablation Purposes and Related Method Thereof" and corresponding U.S. patent application Ser. No. 12/532,233 filed Sep. 21, 2009;

PCT International Application Serial No. PCT/US2010/033189, filed Apr. 30, 2010, entitled "Access Trocar and Related Method Thereof";

PCT International Application Serial No. PCT/US2008/082835, filed Nov. 7, 2008, entitled, "Steerable Epicardial Pacing Catheter System Placed Via the Subxiphoid Process," and corresponding U.S. patent application Ser. No. 12/741,710 filed May 6, 2010;

PCT International Application Serial No. PCT/US2010/061413, filed Dec. 21, 2010, entitled "System For Femoral Vasculature Catheterization and Related Method; and PCT International Application Serial No. PCT/US2011/025470, filed Feb. 18, 2011.

BACKGROUND OF THE INVENTION

Interest in epicardial (outer wall of the heart) treatment of ventricular cardiac arrhythmias has grown significantly within electrophysiology. The thickness of the myocardial wall makes it difficult to treat all heart rhythm problems endocardially (from inside the heart). Although early (pre-reperfusion era) data suggested that epicardial ventricular tachycardia (VT) occurred in a minority of patients, recent (non-ischemic VT and rapid reperfusion era) data suggests that about 70% of VT patients have epicardial substrates for the disease. Several studies have suggested that epicardial ablation procedures are not only a viable second line of defense when endocardial methods fail, but that epicardial procedures should be performed in concert with all endocardial treatments to guarantee the greatest probability of treatment success of both ventricular tachycardia (which kills 500,000 Americans per year) and atrial fibrillation (which is the largest cause of strokes in the U.S.). The epicardial surface is also considered to be an important potential therapeutic location for drug and cell delivery and as well as for heart failure therapy.

The ability to gain minimally invasive access to the heart's outer wall for ablation and other therapies has done much to promulgate the adoption of epicardial strategies.

However, conventional types of guidance methods lead to an unacceptable and high risk of perforations of the RV tissue. For instance, Sosa and Scanavacca had an initial perforation rate of 8%, which decreased to 4.5% with experience. Others using this approach have experienced 12% unsuccessful pericardial access, with pericardial effusion in 13 of 35 cases and one death from complications. Still another study suggested that 10 to 20% of all patients undergoing pericardial access for epicardial ablation using the methods described above experienced effusions due to some level of ventricular perforation.

Therefore, it is a goal of an aspect of an embodiment of the present invention to, among other things, improve the method of access and reduce the risks of its use.

BRIEF SUMMARY OF THE INVENTION

Aspects of the present invention may find applicability in systems and methods such as those described in, for example, epicardial electrophysiology and other procedures in which the location of an access needle may be inferred according to the detection of different pressure frequencies in separate organs, or different locations, in the body of a subject.

An aspect of an embodiment of the present invention may provide, among other things, continuous measurements of the pressure-frequency characteristics across the different regions of the thorax. As discussed further herein, data of that type may be used, for example, to determine how the thoracic pressure-frequency waveform changes upon gaining proximity of and then traversing through the parietal pericardial membrane. The inventors have found that it can further be determined if the transition to a two-component (intubation+heartbeat) signal was smooth and gradual, or more abrupt in nature.

Aspects of the present invention may further provide, among other things, improved instrumentation to collect continuous segments of pericardial and non-pericardial pressure-frequency data in vivo, in contrast to the discrete-location measurements. In particular, an exemplary approach incorporates a high precision fiber-optic sensor into the distal tip of the access needle, which may replace the strain gauge sensor acted on by a fluid column within a stationary sheath in an alternative embodiment.

Further aspects of the invention may provide, among other things, an analysis algorithm, method, technique and system designed to process pressure-frequency data so as to identify when the needle's tip had safely entered, for example, the pericardial space.

An aspect of an embodiment of the present invention may, among other objects, reduce the clinical risks associated with minimally invasive subxiphoid access, and thus improving the reliability, safety and efficacy of it in the epicardial treatment of cardiac arrhythmias and other clinical treatment paths involving the pericardium and epicardial surface.

According to aspects of the invention, methods for inferring the location of a needle in a subject may include one or more steps of inserting a needle including a first sensor into a body of a subject, receiving cardiac waveform information of the subject from a second sensor, and receiving pressure frequency information from the first sensor. Embodiments may include distinguishing, by a computer processor, a current location of the needle from another location and/or distinguishing the transition of the needle from a first location to a second location, based on an algorithm including the pressure frequency information and the cardiac waveform information.

Embodiments may include determining a reference phase based on the cardiac waveform information and/or determining a test phase based on the pressure frequency information. In embodiments, the distinguishing of location, and/or movement, of the needle may be based on the pressure frequency information from the test phase and the cardiac waveform information from the reference phase.

In embodiments, the distinguishing of location, and/or movement, of the needle may include comparing the algorithm results of the pressure frequency information and the cardiac waveform information to a plurality of predetermined threshold values.

In embodiments, the combining of the pressure frequency information and the cardiac waveform information may include phase sensitive detection and matched filtering.

In embodiments, the combining of the pressure frequency information and the cardiac waveform information may include integrating the pressure frequency information.

In embodiments, the reference phase may be a cardiac phase of the subject immediately preceding the test phase. In embodiments, the cardiac waveform information may include information derived from a plurality of cardiac phases of the subject.

In embodiments, the cardiac waveform information may include at least one of ventricle pressure, arterial pressure, pulse oximetry, and electrocardiogram (ECG) signals.

In embodiments, the current location may be a non-pericardial location and the other location may be a pericardial location, or vice-versa. In embodiments, at least one of the current location and the other location may be a thorax of the subject.

Embodiments may also include distinguishing between a location remote from the pericardium, a location close to or in contact with the pericardium, and a location inside the pericardium.

Embodiments may also include identifying a location within ventricular tissue of the subject or inside the interior of the heart of the subject.

According to further aspects of the invention systems for accessing one or more locations of a subject may also be provided. Such systems may include, for example, a needle having a distal end and a proximal end and a first sensor in communication with the needle for sensing pressure frequency in the one or more locations of the subject. Embodiments may further include a processor configured to perform various steps, such as those discussed above. For example, in embodiments, a processor may be configured to receive cardiac waveform information of the subject from a second sensor and receive pressure frequency information from the first sensor. The processor may be further configured to distinguish a current location of the needle from another location, and/or the movement of the needle from one location to another, based on an algorithm including the pressure frequency information and the cardiac waveform information.

The processor may be further configured to determine a reference phase based on the cardiac waveform information, and/or determine a test phase based on the pressure frequency information. The processor may be further configured to distinguish the location and/or movement of the needle based on the pressure frequency information from the test phase and the cardiac waveform information from the reference phase.

In embodiments, the processor may be configured to compare the algorithm results of the pressure frequency information and the cardiac waveform information to a plurality of predetermined threshold values.

In embodiments, the processor may be configured to combine the pressure frequency information and the cardiac waveform information using phase sensitive detection and matched filtering.

In embodiments, the processor may be configured to integrate the pressure frequency information as part of the combining of the pressure frequency information and the cardiac waveform information.

In embodiments, the processor may be configured such that the reference phase is a cardiac phase of the subject immediately preceding the test phase.

In embodiments, the processor may be configured such that the cardiac waveform information includes information derived from a plurality of cardiac phases of the subject.

In embodiments, the processor may be configured to receive cardiac waveform information including at least one of ventricle pressure, arterial pressure, pulse oximetry, and electrocardiogram (ECG) voltages.

In embodiments, the processor may be configured to distinguish between a non-pericardial location and a pericardial location, a pericardial location and a thorax of the subject, and/or between a pericardial location and a location within ventricular tissue of the subject or inside the interior of the heart of the subject.

An aspect of an embodiment of the present invention provides a system for an access needle sensor device that serves as a guideway for introducing other devices into the pericardium, for instance sheath catheters that might subsequently be employed for procedures in the pericardium and the epicardium of the heart. Other devices that the present invention device may accommodate include, but not limited thereto, the following: ablation catheters, guidewires, pacing leads, pacing catheters, pacemakers, visualization and recording devices, drugs, lumens, steering devices or systems, drug or cell delivery catheters, fiber endoscopes, suctioning devices, irrigation devices, electrode catheters, needles, optical fiber sensors, sources of illumination, vital signs sensors, and the like. These devices may be deployed for procedures in an integral body part or space.

An aspect of an embodiment may include, but not limited thereto, approaches to visualize tissues via an imaging-equipped epicardial access needle during insertion and passage of it towards the heart, such as the image capture camera being integral to the distal tip of the needle, or outside of the needle with a coherent fiber optic bundle used to convey the optical signal to it from the distal tip.

In some examples, a very small camera may be used, fitting inside the access needle. In examples, the image at the proximal end of the fiber optic bundle may be magnified by a fiber-optic beam expander in order to provide a useful image for detection by the camera. The beam expansion process may or may not require image intensification, e.g. depending on the initial brightness of the target tissues.

A miniature camera may be, for example, fixed inside the distal end of the lumen of the access needle, or it might be integral to an obturator that can be slid into the lumen of the access needle. In either case, a flow channel may be used through which saline or some other liquid can be pumped, e.g. in order to clear debris from the camera aperture.

In some examples, a fiber optic bundle may be fixed inside the lumen of the access needle, or it might be situated inside an obturator that can be slid into the lumen of the access needle. A flow channel for clearing the input aperture of the fiber optic bundle may also be used for this case as well.

Embodiments may include illumination of the target tissues in order to visualize them. This could be done, for example but not limited thereto, by passing a light beam down one or more optical fibers extending along the length of the access needle (either positioned inside it or perhaps arrayed in a fixed configuration on the outside of the shaft). An LED, a laser diode, or some other suitable source of white light may be used to drive the illumination fibers. It may have a separate control for intensity of illumination.

According to further aspects of the invention, a device for inferring the location of a needle in a subject may be provided including a first input configured to receive pressure frequency information from a first sensor and a second input configured to receive cardiac waveform information of the subject from a second sensor. In embodiments, the first sensor may be disposed proximate to a distal end of the needle. Embodiments may further include a processor in communication with the sensors, the processor configured to perform steps such as those discussed above. For example, the processor may be configured to receive cardiac waveform information of the subject from the second sensor via the second input and/or to receive pressure frequency information from the first sensor via the first input. In embodiments, the processor may be configured to distinguish a current location of the needle from another location, and/or distinguish movement of the needle from a first location to a second location, based on an algorithm including the pressure frequency information and the cardiac waveform information.

In embodiments, the processor may be further configured to determine a reference phase based on the cardiac waveform information, and determine a test phase based on the pressure frequency information. The distinguishing may be based on the pressure frequency information from the test phase and the cardiac waveform information from the reference phase.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention claimed. The detailed description and the specific examples, however, indicate only preferred embodiments of the invention. Various changes and modifications within the spirit and scope of the invention will become apparent to those skilled in the art from this detailed description.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced. In the drawings:

FIGS. 2A-2B show the ECG waveform segmentation. An example ECG waveform (FIG. 2A solid line) is shown, as well as the resulting segmentation points at the R wave (FIG. 2A dotted line). The processed ECG according to the algorithm, method, and technique in FIG. 1 is shown as well in FIG. 2B.

DETAILED DESCRIPTION OF THE INVENTION

Figure 1:
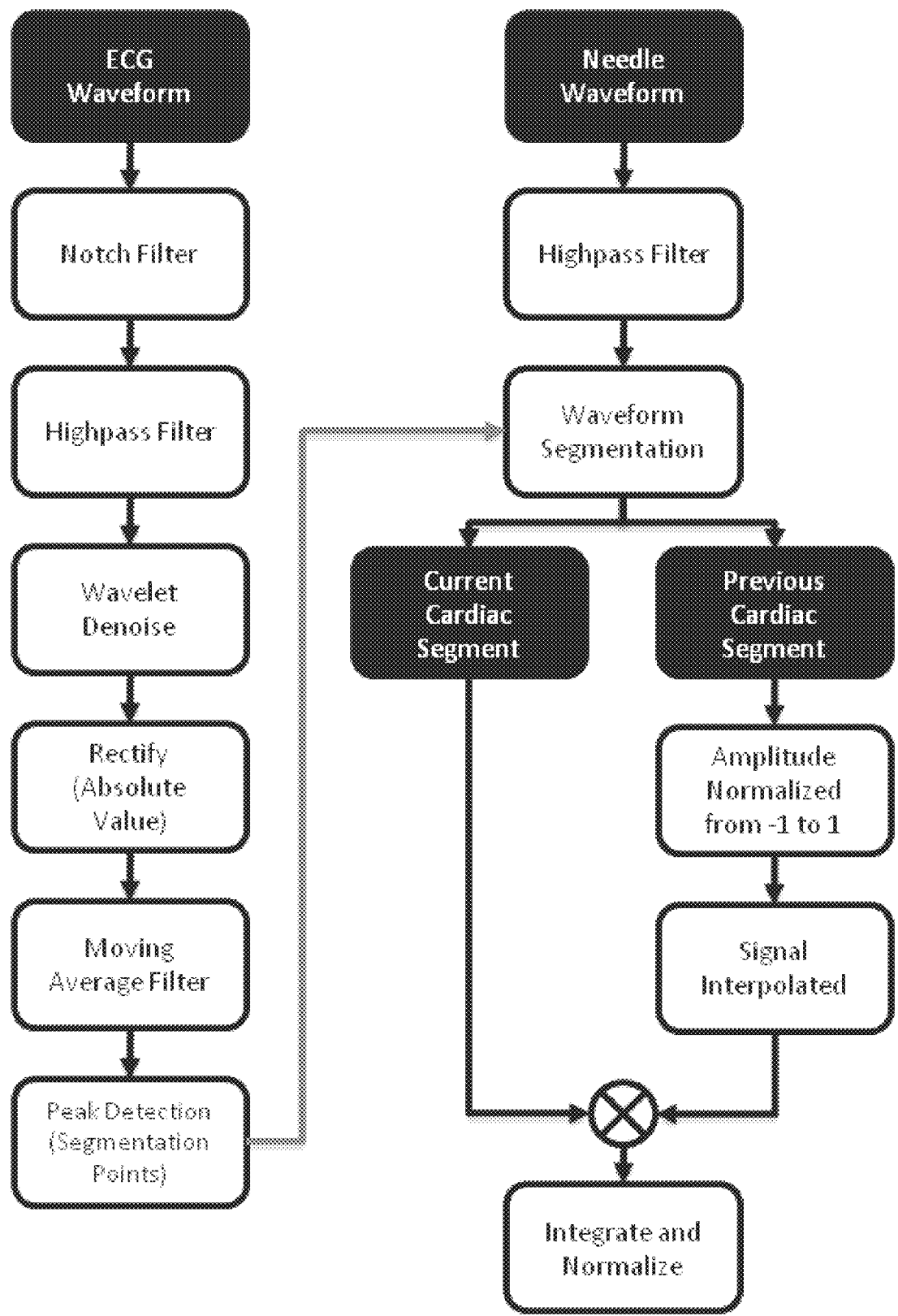
FIG. 1 shows a chart of novel software algorithm, method, and technique steps. Two parallel paths denote the analysis of the reference waveform (left) and the input needle waveform (right).

It is understood that the invention is not limited to the particular methodology, protocols, and configurations, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a sensor" is a reference to one or more sensors and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Although various embodiments may be described in the context of a subxiphoid access, and epicardial treatment, for clarity, the invention encompasses and may be applied to other types of treatment, particularly those taking place in, proximate to, and/or or penetrating tissue or organs of the body including different pressure frequency characteristics.

An aspect of an embodiment of the present invention system (and related method) includes a precision fiber-optic pressure sensor and a novel signal analysis algorithm, method, technique and system for identifying pressure-frequency signatures which, in the clinical setting, may allow for safer access to, for example, the pericardial space.

As discussed further below, aspects of the invention include instrumentation constituting the improved subxiphoid access system, as well as the structure of the data analysis algorithm, method, technique and system. Test results of the use of such systems and methods are also provided based on a series of institutionally approved in vivo trials of the intra-thoracic navigation of the tip of a pressure-frequency sensing Tuohy needle in adult canines. The inventors have further assessed the ability to limit the number of residual false positive and false negative identifications of needle location within the pericardium, as compared with the empirical method as employed in the trials by a practicing electrophysiologist.

Instrumentation

A series of ACUC approved animal trials were performed in the University of Virginia vivarium by a practicing electrophysiologist on ten canines (>22 kg), using the standard-of-care pericardial access techniques currently employed in the clinical Electrophysiology Lab. Anesthesia was induced using fentanyl and etomidate, and maintained with isoflurane. Canines were mechanically ventilated at a constant rate for the duration of the trials, between 13 and 16 breaths per minute. For each animal, a minimum of 4 pericardial access procedures were performed with a standard 17 gauge epidural (Tuohy) needle. The clinician guided it to the pericardium by fluoroscopy and injection of contrast agent. In selected procedures the final pericardial location was verified by placing a guide wire through the access needle's lumen and observing its location under fluoroscopy. Hydrodynamic pressure data from the access needle (>10 s records) were acquired during each procedure at locations intra-thoracic prior to the diaphragm, intra-thoracic after puncturing the diaphragm, and intra-pericardial. The location of the needle, and therefore our determination of each signal's pericardial or non-pericardial nature, was identified by the clinician's judgment. Some of the data were taken with the needle held in static positions, and the rest while it was being moved from the thoracic cavity into the pericardium, as well as upon withdrawal. Certain pressure recordings were made with ventilation held to anatomically remove breathing signals from the waveform.

During the access procedures, four simultaneous measurements were acquired on a laboratory computer using LabVIEW SignalExpress™ (National Instruments, Austin, Tex.). The four measurements included the pressure as monitored by the sensor in the needle's tip, the left ventricle (LV) pressure, the right femoral artery (A-line) pressure, and the electrocardiogram (ECG) voltages.

In an initial study of pericardial pressure dynamics, a strain gauge on the proximal end of the access needle was used to sense the pressures at the distal tip via a column of fluid between it. Although such instrumentation is highly effective when utilized properly for reading static pressure measurements from a single location, it is difficult to employ for reading small-amplitude hydrodynamic pressures when the fluid-filled conduit (be it a sheath, catheter, or needle) is moving. This is because the fluid filled column has weight, and hence the fluid's hydrostatic pressure contributes inertial artifacts to the amplitude of the pressure read at the proximal end of the fluid conduit. If the needle's orientation relative to gravity is not maintained unchanged while it is being advanced towards the pericardium, the resulting fluctuations in the force transduced by the strain gauge introduce substantial noise onto the signal. This makes the technique very difficult to employ in the clinical setting during an access procedure.

Therefore, a more viable method of monitoring pressures at the tip of a dynamically shifting access needle is desired. In embodiments, exemplary systems may include a solid-state, or optical, pressure sensor. As used herein, "pressure sensors" may preferably include sensors that are capable of registering not only steady-state pressure, but also pressure frequency over time, which may require rapid responsiveness and accuracy. In embodiments, such sensors may also be understood as including, and/or in communication with, a computer processor configured to determine pressure frequency from pressure signals. Varying pressure information received over a period of time may also be referred to generally as pressure frequency information.

A fully solid-state sensor was implemented by the inventors including a fiber optic (Fabry-Perot resonator) pressure transducer (FISO, model FOP-MIV-BA-C1-F2-M2-R1-SC, Quebec, Canada), and was introduced into the lumen of an access needle, with the transducer tip placed just within the edge of the distal tip of the needle so that it did not protrude into the tissue. The sensor at the distal tip of the fiber had a diameter of 550 µm. This was followed by a 20-mm segment of bare fiber of roughly half the sensor's diameter, with the remaining length encased in a PTFE sheath all the way to the connector at the proximal end. The resolution was ≈0.3 mm Hg, with a residual thermal drift of $<-0.05\%\ °C.^{-1}$. In embodiments, a pressure sensor, such as an optical sensor, may be affixed to, or proximate to, an end of an access needle. As discussed further below, securing the pressure sensor may be advantageous in reducing unwanted noise, but is not necessarily required.

The optical fiber itself was fixed in place at the proximal end of the needle by passing it through a Tuohy-Borst adapter which was coupled onto the needle's Luer lock. In this instance, the transducer was not fixed at the tip of the needle, since it had to be removed from the inner lumen so that a guide wire could be passed through the needle to verify the location inside the pericardium. This was accomplished by decoupling the Tuohy-Borst fitting from the needle's Luer lock and withdrawing the sensor. During use, the fiber optic cable was connected to its mating light source/signal conditioning device (FISO, model EVO/FPI-HR, Quebec, Canada). The voltages from the analog output board on the signal conditioner were read by an analog-to-digital data converter (National Instruments, model USB-6009, Austin, Tex.) and stored for subsequent analysis.

As mentioned above, three standard measures of cardiac dynamics were acquired in synchrony with the needle pressures during each trial. First, the LV pressures were monitored via a clinical pigtail catheter, which was inserted into the left ventricle from the animal's carotid artery. The pigtail catheter was flushed and filled with saline, and the pressure in it was monitored by a clinical flush-through transducer (Hospira, model Transpac™, Lake Forest, Ill.). Second, central A-line pressures were obtained via a 10 French sheath, placed in the femoral artery of the canine. The sheath was flushed and filled with saline, and monitored by a transducer identical to that used in the LV pigtail catheter. Both the LV and A-line transducers were connected to a data acquisition and signal conditioning board (National Instruments, model USB-9237, Austin, Tex.) via a custom-built cable that bridged the RJ11 jack of the transducer wiring to the RJ50 input plug on the board. These resulting data were useful in assessing the effect of cardiac dynamics on pericardial pressures.

Third, electrophysiological data were taken during the procedures. The bipolar electrical signal between leads on the right arm (RA) and left arm (LA) was monitored by a custom-built ECG reading system. The ionic potentials were transduced to electronic potentials via standard clinical pediatric ECG electrodes (Ambu®, model Blue Sensor M, Glen Burnie, Md.). The RA and LA leads were connected to a custom-built, differential-amplifier signal conditioning circuit (Burr-Brown/TI model OPA2227 P operational amplifiers, Dallas, Tex.) to buffer, amplify, and bandpass-filter the incoming signal. The output signal from the circuit was connected to the second port of the A/D data acquisition device. The signals from both data acquisition units were transferred to the laboratory computer via USB 2.0 connections at a rate of ~1.6 kHz by the LabVIEW SignalExpress™ software.

Data Processing

Fast Fourier Transform Analysis. For each canine, a set of non-pericardial (pre-diaphragm and post-diaphragm thoracic signals) and intra-pericardial signals were collected. These signals were examined for segments with minimal noise, and suitable samples 10 s long were extracted for further analysis. A hanning window was applied to the segment, and a linear-peak Fast Fourier Transform (FFT) was carried out in LabVIEW. Using the embedded virtual instrument functions on the same 10 s segment of any of the cardiodynamic reference signals, the average heartbeat frequency for that segment was calculated, and the magnitude of the FFT at that specific frequency point was identified as the signal magnitude of interest at the heart rate. Altogether, 98 non-pericardial and 112 pericardial signals were collected and analyzed in this manner.

Following the collection of signal-magnitude data from all 210 signals, an automated search was performed to determine how well a threshold value of the cardiac signal strength at the heart-rate frequency could separate pericardial from non-pericardial locations of the needle tip. A custom program in MATLAB® was written and used to numerically evaluate the magnitude data. The frequency component at the heart rate is significantly less in the non-pericardial signal when compared to the pericardial signal. The goal then was to define a threshold pressure which indicated the best obtainable separation between non-pericardial and pericardial signals by inferring the presence of false positives and false negatives (i.e., non-pericardial signals above the threshold, denoted by $false_p$; pericardial signals below the threshold, denoted by $false_n$, respectively). Possible threshold values were tested from the range of 0 to 0.6 mmHg (0 to 80 Pa), in increments of 0.0001 mmHg (0.013 Pa). For each possible threshold value within that range, the number of non-pericardial signal magnitudes above that threshold (false positives) and the number of pericardial signal magnitudes below that threshold (false negatives) were counted. The best obtainable threshold was then found by minimizing the score $$\text{Score} = W_p * false_p + W_n * false_n \quad (1)$$

where the scoring weights $W_p$ and $W_n$ indicated the relative importance of false positives and false negatives. In a given calculation for best obtainable threshold, $W_p$ and $W_n$ remain constant. A best obtainable threshold was found for every combination of values of $W_p$ and $W_n$ ranging from 0.1 to 1.0 in increments of 0.1. The nature and application of the findings is discussed below in the Results Section.

Custom Algorithm and Method Analysis. Additional investigations were conducted for determining if a cardiac signal was present in the needle-tip signal, taking into account the inconsistency of the heart rate in many of the experiments and, in general, the spectral complexity of the heartbeat signal. For example, heart-rate variability could not only cause FFT spectral leakage, but even separate the FFT cardiac peak into distinct sub-peaks of lower magnitude, making FFT-based measurements inconsistent. Using the ECG as a reference signal, the needle sensor's waveform was segmented between consecutive R waves in the QRS complex of the signal. A custom-synthesized algorithm that combined aspects of phase sensitive detection (PSD) and matched filtering then analyzed it to ascertain the presence of a consistent waveform with a fundamental frequency at that of the heart rate, but with the ability to accommodate beat-to-beat variations in heart rate. A flow chart for this algorithm is shown in FIG. 1.

Figure 3:
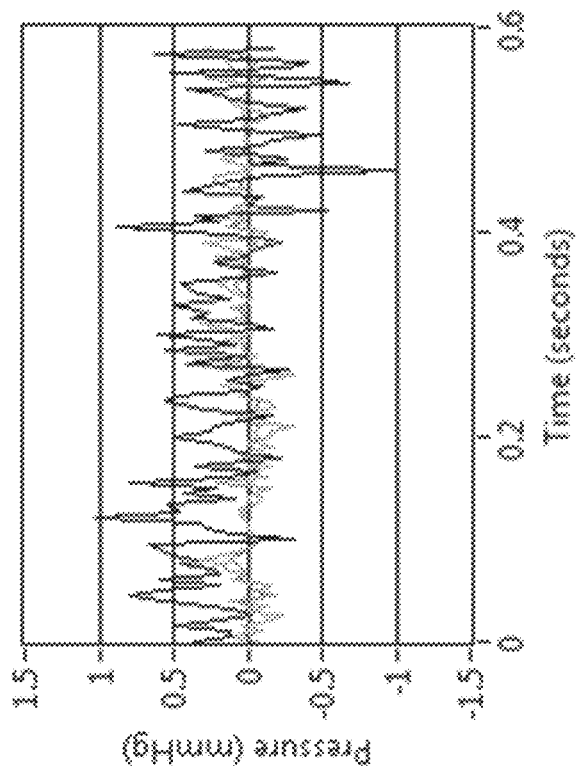
FIG. 3 shows the algorithm and method signal analysis. Pericardial (left) and non-pericardial (right) examples of the analysis of cardiac signal segments. Current cardiac segment (G), previous cardiac segment interpolated and normalized (B), and multiplied signals prior to integration (R).
Figure 3:
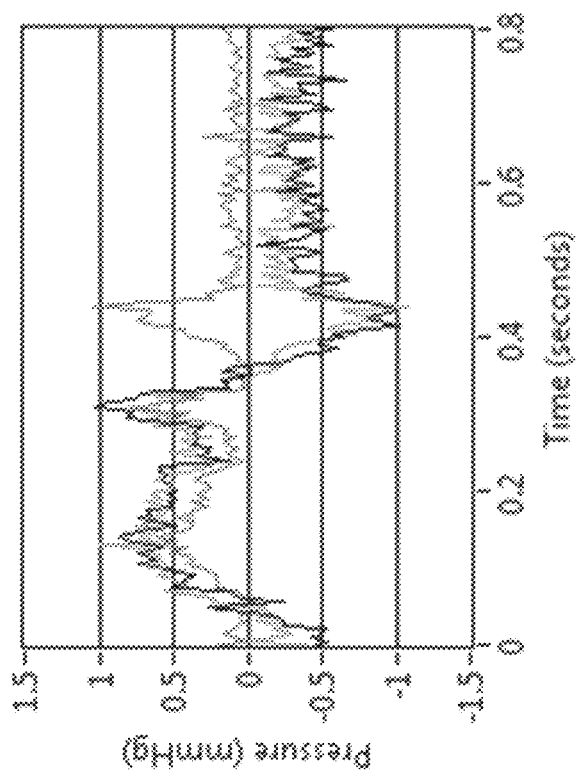

In FIG. 1, two parallel paths denote the analysis of the reference waveform (left) and the input needle waveform (right). Boxes are labeled as either a signal processing step (white background) or a waveform (shaded background). The functions of the blocks/elements in FIG. 1 are explained in detail below, and FIGS. 2 and 3 show the nature of the operation of the algorithm as the data stream progresses through the blocks/elements of FIG. 1.

For the algorithm and method analysis, the same signals from the FFT analysis were used for the algorithm and method analysis, and an automated program in LabVIEW performed it on each of the needle sensor's waveforms. After reviewing the spectral structure of all the types of waveforms that were captured, none of which contained signal components≥100 Hz (which was taken to be the Nyquist frequency), the signals were down-sampled to 2×100 Hz=200 Hz to allow for more precise filtering. All filtering routines were performed in a zero-phase implementation, infinite impulse response (IIR) mode, which filtered the forward signal and then reversed and refiltered it, and reversed it again in order to remove all phase-sensitive filtering transients. Moreover, all of the simple high- and low-pass filters were of elliptic structure in order to minimize the order of the filter, thus both minimizing start- and end-signal transients and maximizing the computational efficiency.

Reference Waveform Segmentation

The ECG waveform served as the reference for the algorithm and method in identifying the timing of cardiac cycles in the animal. The ECG signal segment was notch-filtered at 60 Hz ($Q \approx 50$) to eliminate any residual power-line noise that the signal conditioner did not fully remove. The signal was then high pass-filtered at a cutoff frequency of 20 Hz, to maintain only the high frequency elements that compose the QRS complex. Then, the strength of the remaining high-frequency noise components were attenuated with an undecimated wavelet transform using a biorthogonal 4_4 (FBI) wavelet to insure that only the QRS peak of interest remained. To provide for consistency in subsequent mathematical steps, the signal terms were then rectified by their absolute value and the remaining detectable but extraneous peaks were smoothed with a moving average filter. As shown in FIG. 2, the surviving peaks were then identified as the R complex or the center of the QRS complex in the cardiac cycles, in order to segment the waveform into heartbeats according to the electrophysiology of the patient.

FIG. 2 shows the ECG waveform segmentation. An example ECG waveform (top, solid line) is shown, as well as the resulting segmentation points at the R wave (top, dotted line). The processed ECG according to the algorithm, method, and technique in FIG. 1 is shown as well (bottom).

Analysis of the Pressure Waveform Produced by the Needle's Sensor

The 10 s records of the needle's hydrodynamic pressure signal were high-pass filtered with a cutoff frequency of 1 Hz to attenuate low frequency breathing components. The resulting signal was further separated into cardiac segments according to the timing points found using the ECG analysis above. Only cardiac segments containing a full cardiac cycle (a start and an end point) were analyzed. A goal of the algorithm and method was to quantitatively compare the waveform between consecutive cardiac segments. In many implementations of phase-sensitive detection, the input waveform is multiplied by a reference signal in order to evaluate whether the waveform is of the desired frequency and phase. If the input waveform's characteristics match those of the reference waveform, then the multiplied signal will be perfectly rectified. For reasons discussed below, in place of a common reference waveform which would be used for that multiplication, the algorithm instead used an interpolated version of the previous cardiac segment as the reference waveform for the currently analyzed cardiac segment. Examples of both pericardial and non-pericardial signals are shown in FIG. 3.

FIG. 3 shows the algorithm and method signal analysis. Pericardial (left) and non-pericardial (right) examples of the analysis of cardiac signal segments. Current cardiac segment (G), previous cardiac segment interpolated and normalized (B), and multiplied signals prior to integration (R). Prior to that multiplication, the previous cardiac segment was normalized to fit between ±1 to insure uniformity of reference scale size. Then, the area under the resulting signal segment was integrated to arrive at an exact measure of the level of signal rectification. A high positive output of the integration step correlated to a significant signal with a fundamental frequency at the heart rate, while other signals integrated towards zero. Because of the time dependency of the integration process, the integrated output was then multiplied by the fundamental frequency of that segment for normalization in the time domain. A signal which is of higher frequency will have a shorter integration time, and this is why the integration is normalized by the frequency of the segment. The outputs for each cardiac segment were then averaged over the 10 s signal window. Algorithm thresholds were found using the same scoring function as that employed for the FFT data as described above.

This routine combines features of both match filtering and PSD. If the main signal component which is present is fundamentally matched to cardiac dynamics, then the signal should repeat between cardiac segments, regardless of noise. It is assumed that if the needle is in the pericardial space, then there should be good agreement between the current and last cardiac segment of the waveform. However, instead of convolving the signals or performing Fourier multiplication of the signals, which is computationally inefficient or requires a large window of consistent repeatable signal, respectively, the signal may be integrated.

Another significant point is that when integrating a high-noise signal, as more time points are integrated, the integral of white noise tends to zero. Hence, this algorithm and method also functions efficiently in high noise scenarios. In summary, this approach, which employs the ECG as the reference waveform, is a more elaborate but robust way of ascertaining the presence and magnitude of a cardiac signal pattern in the needle sensor's pressure signal, which can take into account and adjust for irregular or inconsistent heart rates.

Results

Average Signal Output

The signal magnitude at the heart rate frequency of the FFT of the 98 non-pericardial waveforms was (0.09±0.08) mmHg, and it was (0.55±0.31) mmHg for the 112 pericardial signals. Unpaired, one-tailed t-tests revealed a statistically significant difference in means of the two groups (p<0.01). Purposeful ventricular perforation was successful in 5 animals, and the mean signal at the heart rate from these 5 measurements was (24.98±9.34) mmHg, which was significantly greater than the magnitudes for both the non-pericardial and pericardial groups (p<0.01).

Figure 4:
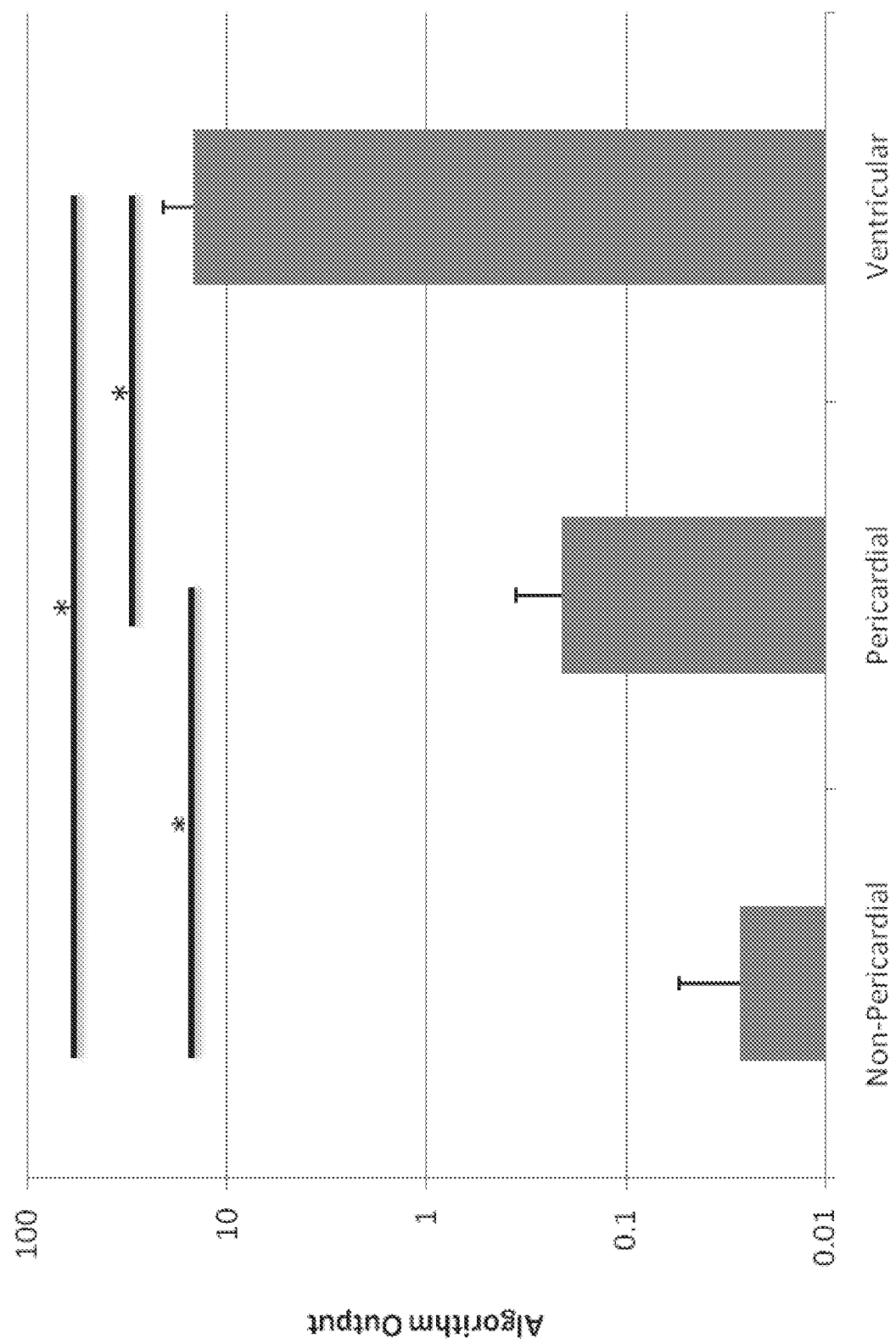
FIG. 4 shows the average (dimensionless) test output values for all 98 non-pericardial, 112 pericardial, and 5 ventricular signals plotted on a log scale.

The average, dimensionless signal output from the algorithm for the 98 non-pericardial waveforms was (0.024±0.03), and (0.21±0.14) for the 112 pericardial signals. Average signal output for ventricular signals was (14.74±5.97). As shown in FIG. 4, all groups are significantly different from each other (p<0.01).

Threshold Signal Separation

Using Eq. (1) on both the FFT and algorithm data, a number of thresholds were found which separated the pericardial from the non-pericardial data. However, this analysis also revealed some overlap of non-pericardial and pericardial signals, i.e., regions of non-separation of the signals (transition zone in FIG. 7). These overlaps in signal strength may have been due to tissue clogs in the needle lumen, imperfect localization of the sensor in or outside of the pericardium, or the presence of a small cardiac signal directly outside the pericardium. The latter-most option is the most likely, especially if the needle is being pushed against the pericardial surface, and therefore is in immediate proximity of the heart. However, this range of signal overlap is important, and suggests a need for three separation thresholds of cardiac signal strength for the pericardial access procedure in the clinical setting. These three thresholds would provide for the clinically relevant separation of four regimes of pressure-frequency signal dynamics: (i) away from the pericardium, (ii) very close to the pericardium (the "transition" zone), (iii) safely inside the pericardium, and (iv) dangerously within the ventricular tissue. Moving from the thorax towards the heart, the first threshold, $T_a$, identifies the beginning of the transition zone, where a small cardiac signal first arises. The second threshold, $T_b$, identifies the beginning of the pericardial zone, where the signal structure is definitively pericardial. The third threshold, $T_c$, would indicate that there has been perforation of the ventricle, which would be associated with a vast increase in cardiac signal strength.

After analyzing both the FFT and algorithm data and method, the values for thresholds $T_a$ and $T_b$ were selected. The number of associated false positives and false negatives are displayed in FIG. 7.

Figures 7, 8:
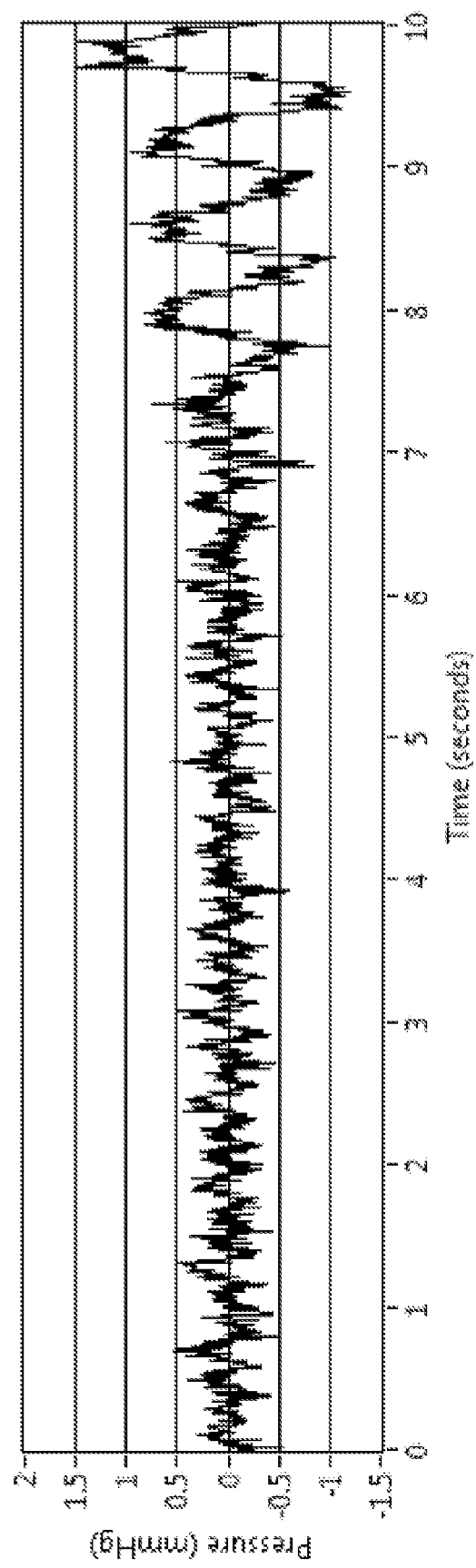
FIG. 7 shows the threshold values and performance characteristics of the algorithm compared to the FFT analysis.
FIG. 8 shows an indication of pericardial access. Incoming signals from the fiber optic sensor in the access needle during a ventilation hold (to suppress the breathing component of the waveform), as the needle is moved through the parietal pericardial membrane and into the pericardial space. An abrupt shift in the frequency characteristics of the pressure signal becomes apparent upon entry into the pericardium, as a large temporal signal fluctuating at the frequency of the heart rate appears.

FIG. 7 shows the threshold values and performance characteristics of an exemplary algorithm compared to the FFT analysis. The exemplary algorithm and method is shown to be more efficient at separating pericardial from non-pericardial signals, as indicated by the decreased number of signals in the transition zone between $T_a$ and $T_b$, as well as the increase in the number of signals which fall above or below the appropriate threshold.

Figure 5:
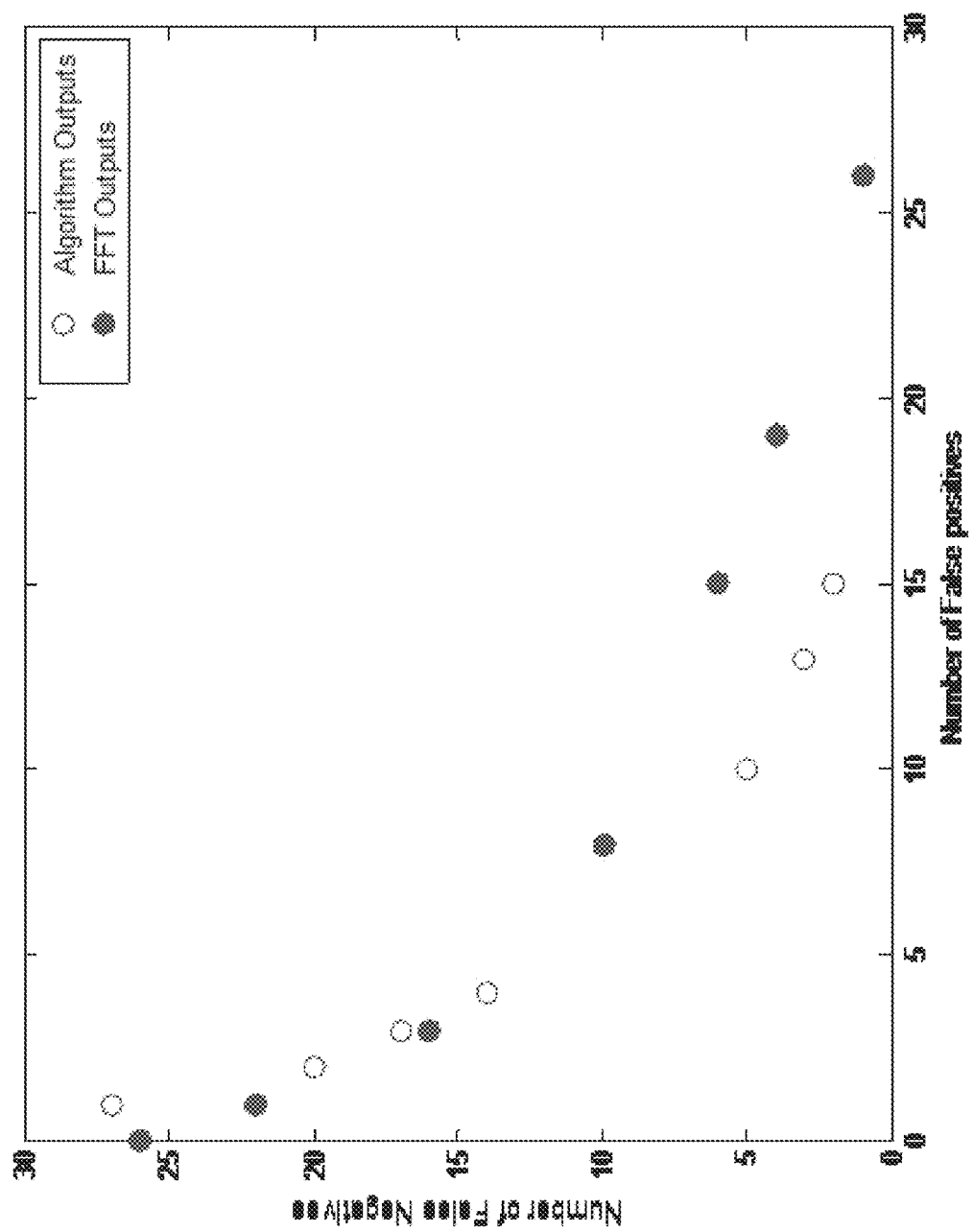
FIG. 5 shows the threshold analysis. The number of false positives plotted against the number of false negatives for a range of different threshold values for the algorithm analysis (open circles) and the FFT analysis (closed circles).

The separation of non-pericardial from pericardial signals is the main focus in what follows. This is because the separation of ventricular from non-ventricular signals is easily achieved for $T_c$ without any false outputs. The performance of both the FFT and algorithm analyses (and related methods) of the data is shown in FIG. 5, which shows their relative abilities to limit both false positives and false negatives over a range of threshold values.

Figure 6:
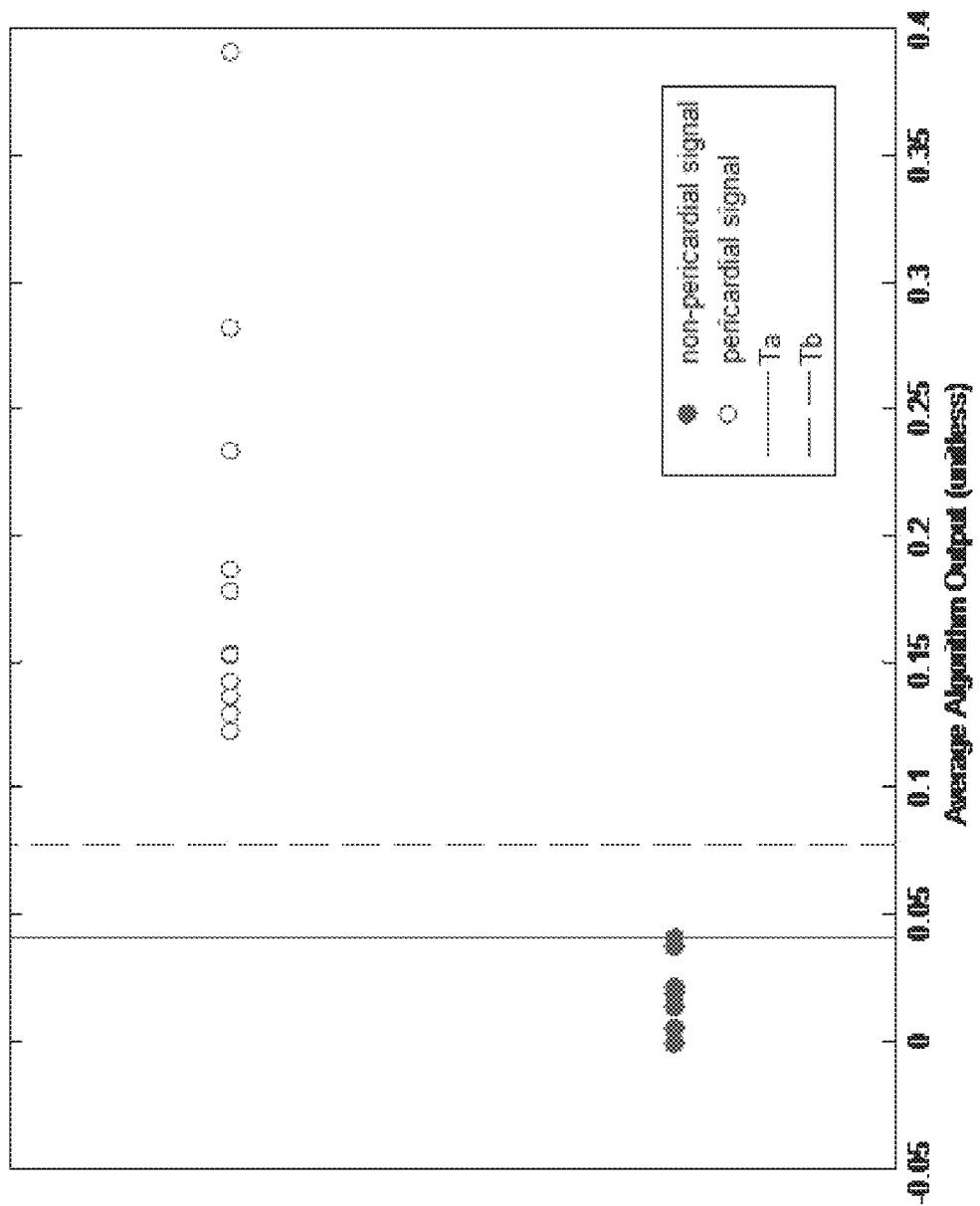
FIG. 6 shows an example of the in vivo data. Algorithm and method output for all signals from one animal, including the output for all pericardial signals (open circles) and non-pericardial signals (closed circles), as well as the presence of the thresholds Ta (solid line) and Tb (dashed line), showing the separation of signals.

False positives are more of a procedural nuisance than a safety concern. On the other hand, false negatives are dangerous, because the clinician might continue to advance the access needle into the ventricle if the needle is actually pericardial but the algorithm indicated that it was instead non-pericardial. Therefore, one object of the invention is to not only minimize the total number of false outputs (of both kinds), but to make the minimization of false negatives the highest priority. The custom-synthesized algorithm is able to minimize the number of false negatives with much fewer false positives (see FIG. 5), making it a more effective tool than FFT analysis for clinical assessment of needle location using pressure-frequency guidance. See Table I for representative values of $T_a$ and $T_b$, and see FIG. 6 for a plot of the signal outputs found for one of the animals.

The resulting threshold values in the algorithm are 0.0405 for $T_a$, 0.077 for $T_b$, and 4 for $T_c$. Of the 210 non-ventricular pressure measurements, 87.14% of the acquired signals fell in the appropriate zone upon analysis with the algorithm, with 1.43% of the signals identified as false negatives, 1.90% of the signals identified as false positives, and 9.52% of the signals in the transition zone between $T_a$ and $T_b$. All 5 (100%) ventricular measurements fell above $T_c$, with no false negatives or false positives regarding signals falling on the wrong side of $T_c$.

It is important to address the pericardial signal outputs which fall beneath both $T_a$ and $T_b$ (i.e., the false negatives shown in FIG. 7). Using an exemplary algorithm and method, one of the false negatives from the FFT analysis was remedied, because the algorithm was able to take into account the complexity of the pericardial signal, while the FFT approach could not. While there were still three false negatives assigned by the algorithm, the inventors found that all were caused by the presence of a large number of pre-ventricular contraction (PVC) beats. Although the algorithms and methods used in this case were efficient at handling solitary PVC beats in a given window, in each of the three instances of false negatives the majority of the waveform was composed of PVC beats. These beats caused lengthy inconsistencies in the cardiac dynamics, making all of the pressure-signal dynamics inconsistent as well. In all three instances of false negatives for the algorithm, the time before the signal is PVC-free, and the signal output occurs above $T_b$ in the appropriate signal zone. This proved that these signals were anatomically pericardial, but that the inconsistent cardiac dynamics caused by the PVCs were impossible to track.

Thus, it was noted that it is possible that solitary PVC beats may cause an error in the algorithm and method if only one previous beat is used for comparison to the current cardiac segment. In embodiments, such errors may be avoided, for example, by adapting the algorithm to compare, for example, the previous two to five beat segments. There are several ways in which it might be accomplished, e.g. by acquiring and averaging the parameters of two neighboring PVC beats and using that result to drive the segmentation of the needle waveform. Other criteria may be applied to disregard a reference phase. Such criteria may rely, for example, on an appropriate statistical measure used to identify a significantly irregular beat pattern (e.g., a sudden change in the frequency band in which the beat occurred, indicating the occurrence of what in nonlinear dynamics is called a "transition to chaos").

In embodiments, the algorithm may be adapted to focus primarily on capturing the first cardiac segment once the needle is positioned pericardially. If one PVC beat were to occur at that first segment, then the algorithm would simply have a delayed response of one extra cardiac segment, and the probability of a PVC occurring at such a precisely defined moment is very low.

Pericardial access can be critical for curing several cardiac conditions but it is fraught with a high risk of both procedural failure and ventricular perforation. To address these issues, the inventors measured the pressure-frequency signals generated by a solid state (fiber optic) sensor at the tip of a pericardial access needle, and collected ECG signals in synchrony. By employing a novel algorithm, method, technique and system that contains characteristics of both matched filtering and phase-sensitive detection to process those data, the location of the needle's tip was distinguished accurately. In analogy with phase sensitive detection, the present subject matter uses measures of cardiac dynamics to separate the incoming needle's signal into distinct sections. Also, just as matched filtering checks an incoming signal according to a known outgoing signal, exemplary algorithms according to aspects of the invention may be configured to compare the current cardiac section of the signal to the previous section, to search for a similar pattern. Such algorithms, and associated methods, techniques and systems, can distinguish pericardial from non-pericardial waveforms regardless of signal dynamics and structure, as long as a signal with the fundamental frequency (equal to the cardiac frequency) is present at any given time. This is significant, because as different parts of the pericardium are accessed at different needle insertion angles, the signal structure can change.

It was found that the exemplary algorithms, and associated methods, techniques and systems, presented herein provided a better approach than tracking an FFT peak for several reasons. First, FFT peaks take time to establish in a signal window, since they sample global (and not local) frequency content. However, use of an exemplary algorithm in systems such as those described is expected to decrease the time lag needed to establishing the needle's presence in the pericardium to just one cardiac cycle (i.e., ~1 s).

In order to achieve such results, it is expected that a sensor fixed, or locked, proximate to the end of the needle would be advantageous. That is, configurations in which the fiber optic sensor is left un-fixed within the tip of the needle (e.g. so that it can be easily extracted whenever a guide wire had to be passed into the needle's lumen), may result in some mechanical noise being imposed on the signal based on the residual motion of the sensor's tip. In order to reduce the overall effect of such noise, the algorithm's output may also be averaged over an extended window.

Also, as the patient's heart rate undergoes normal shifts, both spectral leakage and separation of FFT peaks is a concern. Since the systems and methods described herein track the patient's cardiac dynamics directly, embodiments may also provide means of tracking heart rate during accelerations into tachycardia, decelerations into bradycardia, and inconsistencies as occur in atrial fibrillation. Also, embodiments of the invention may be useful for patients with low cardiac signal strength in the pericardial waveform because of previous cardiac surgery and the resulting pericardial adhesions.

Another important aspect of the invention is to quantify the pressure waveform at the needle's tip as it breaches the pericardial membrane, going from non-pericardial to pericardial anatomy. In studying this, the inventors looked at several examples of dynamic pressure measurements made while the needle both breached into the pericardium and was pulled out of it were acquired, and an example is shown in FIG. 8.

FIG. 8 shows an indication of pericardial access. Incoming signals from the fiber optic sensor in the access needle during a ventilation hold (to suppress the breathing component of the waveform), as the needle is moved through the parietal pericardial membrane and into the pericardial space. The signal transition occurs just before the 8 second mark. It is evident that there is a discrete addition of cardiac signal to the waveform at the point of entering/leaving the pericardium. However, it is also evident that there is a transition zone, which most likely occurs as the needle is right outside the pericardium, which contains small levels of cardiac signal, justifying the use of $T_a$, to warn the clinician they may in fact be close to the pericardium, although not intra-pericardial.

According to aspects of the invention, embodiments may also be adapted to allow for the analysis to occur in real time. Such adaptation may include, among other features, real-time data analysis during signal acquisition, as opposed to post-processing of data segments. Also, a statistical analysis of this and other pericardial and non-pericardial signals may be analyzed to determine not clinical thresholds between anatomical zones, as well as determining confidence intervals for those thresholds. This would allow for systems and methods that tell the clinician which anatomical zone they are in with statistical certainty. The needle itself is also an important part of the access system that can be improved to provide real-time or near real-time analysis. The device used by the inventors was a Tuohy epidural needle, but with the fiber optic sensor threaded through the lumen to the tip. However, the pressure sensor was neither fixed to the tip of the needle, nor designed to be otherwise housed by the Tuohy needle, and this allowed the fiber optic tip to move in certain situations, thus increasing noise and decreasing signal fidelity. A needle with, for example, a fixed or locked pressure sensor would be expected to produce readings with a larger signal-to-noise ratio.

As discussed above, following in vivo studies on 10 adult canine models, the inventors analyzed 215 pressure-frequency measurements made at the distal tip of the access needle, of which 98 were from non-pericardial, 112 were from pericardial and 5 were from ventricular locations. The needle locations as identified by the exemplary systems and methods were significantly different from each other ($p<0.01$), and systems and methods showed improved performance when compared to a standard FFT analysis of the same data. Moreover, the structure of the algorithm, method, technique and system can be advantageously used to minimize, or overcome, the time lags intrinsic to FFT analysis, such that the needle's location may be determined in near-real time.

An advantage accruing from the use of the means and method of the invention is, but not limited thereto, the ability to allow for pacing of the epicardium itself with relative ease.

Figure 9:
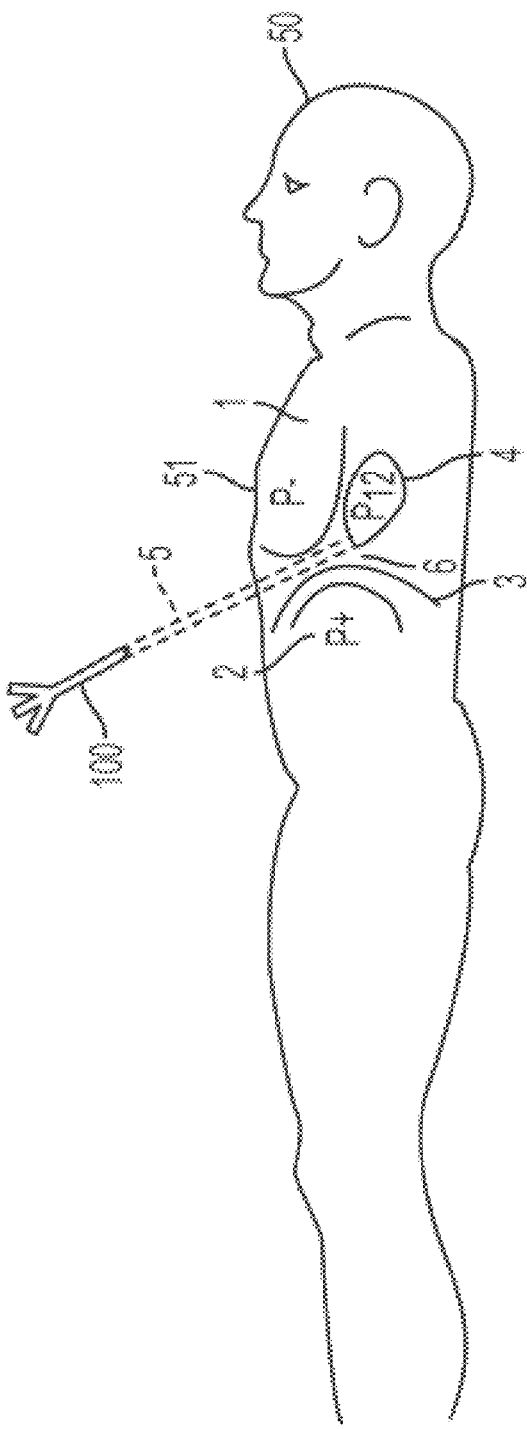
FIG. 9 is an illustration of an exemplary system according to aspects of the invention, as used on a subject.

FIG. 9 shows a human subject 50 undergoing insertion of an access needle 100 into the pericardial region 6 along a desired pathway 5. The access needle 100 may include a pressure (or pressure frequency) sensor disposed proximate to a distal end of the needle. Other sensors (not shown) may also be disposed at or in different locations of the subject 50, such as, for example ECG sensors, and/or ventricle or arterial pressure sensors. The access needle 100 can also be used to access the thorax 51 of the patient 50. The access can be accomplished by an interventional procedure, such as a sub-xiphoid puncture, or a surgical procedure. It is important during the procedure that critical organs and anatomical structures within that region are not damaged by inadvertent insertion of the access needle 100 into them during the needle placement process. The physiological functions of the internal organs, spaces and structures of the body within that region occur at different levels of hydrostatic pressure. For instance, the stomach 2 exerts a positive pressure ($P_+$) on its bounding structures, including the diaphragm 3. Meanwhile, the lung 1 will function at negative pressures ($P_-$) in the range of 5 to 10 atmospheres, with the heart 4 maintaining surface pressures of approximately 12 mm Hg. Therefore, there are a variety of pressures (as well as pressure frequencies) that might be sensed by the access needle 100 during placement of it.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

In an aspect of an embodiment of the invention, the access needle 100 is used for accessing the thorax 51 and pericardium of a subject 50, wherein the access needle comprises a pressure frequency sensor or system for sensing pressure frequency in the thorax, the pericardium or other tissue of the heart. However, it should be appreciated that various embodiments of the present invention device or system and method are not necessarily limited to accessing the thorax and pericardium of a subject. It may also be used in the organ structures or tubular structures in the thorax as well as other locations or regions in the body. An organ includes, for example, a solid organ, a hollow organ, parenchymal tissue (e.g., stomach, brain, esophagus, colon, rectum, kidneys, liver, etc.) and/or stromal tissue. Hollow organ structures includes, for example, stomach, esophagus, colon, rectum, and ducts, or the like. A tubular structure may include a blood vessel. A blood vessel may include one or more of the following: vein, venule, artery, arterial, or capillary.

Figure 10:
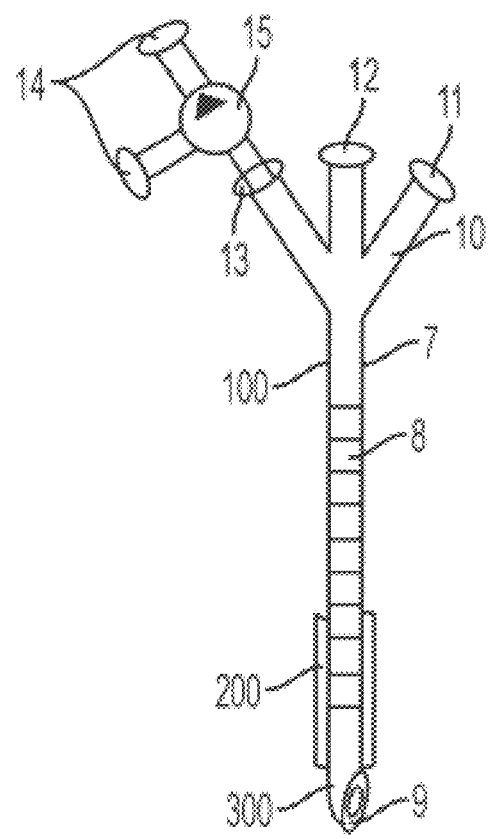
FIG. 10 is a schematic diagram of an exemplary access needle according to aspects of the invention.

FIG. 10 shows a schematic diagram of the details of construction of one embodiment of said access needle 100. The needle 100 has a distal end 300 and a proximal end 7. In some embodiments, the needle 100 will have a length of about 10 to 25 cm and will be of about 14 gauge size, but it could be smaller or larger as suits the anatomy of the patient and the needs of the clinician using it. The needle may have markings 8 nominally at about 1 cm locations along its axial length. The markings can be used to observe the depth of insertion of the needle 100 along the pathway 5 shown in FIG. 9. At the proximal end 7 of the needle, there can be at least one aperture, such as a plurality of channels 10 that provide means for achieving the functionalities of the subject invention. These can include a port 11 to which the manometry or pressure frequency sensing apparatus is connected and/or a port 12 into which a guidewire, sheath, catheter, puncture needle, or other devices or tools that may be inserted for passage through and withdrawal from a distal aperture, such as an end port hole 9. The puncture needle (not shown) can be in communication with a spring and used to puncture tissue of a patient. A port 13 can be connected to a multi-channel structure, conduit or connector, such as a three-way stopcock 15, for example, with inlet ports 14 to allow entry and control of the flows of infusion agents or desired fluid or medium. This flow can include providing a fluid, liquid, gas, or mixtures thereof, with or without therapeutic agents, drugs or the like, heating and/or cooling of the fluid, chemical reactions and/or physical interactions between the components of the fluid, and draining of the fluid. At the distal end 300 of said needle 100, there can be an aperture, such as a beveled end port hole 9. Said needle 100 might serve as the placement mechanism for a sheath or catheter means 200, only the distal portion of which is shown in FIG. 10. In another embodiment, the sheath or catheter means 200 can be placed inside the needle 100. In one embodiment, the needle could have a divider running the length of its axis, thus creating two or more zones, or lumens, within it. One could be used for pressure frequency sensing, while the other could be used for passage of a guide wire, catheter, sheath, or puncture needle or other device or injection of a contrast agent or other medium. The sensing component of the needle could be much smaller in mean diameter than the other component, with the sensing orifice positioned just in front of the other component's orifice (or other locations, positions and sizes as desired or required). As a result, if the sensing component detected a perforation of the right ventricle, the resultant hole created by the puncture devices or the like would thus be small. Moreover, the entire distal tip of the inner needle assembly could also be re-shaped so that it is similar to a Tuohy needle or some other suitable configuration, thus further minimizing the risk of inadvertent perforations.

Figure 11:
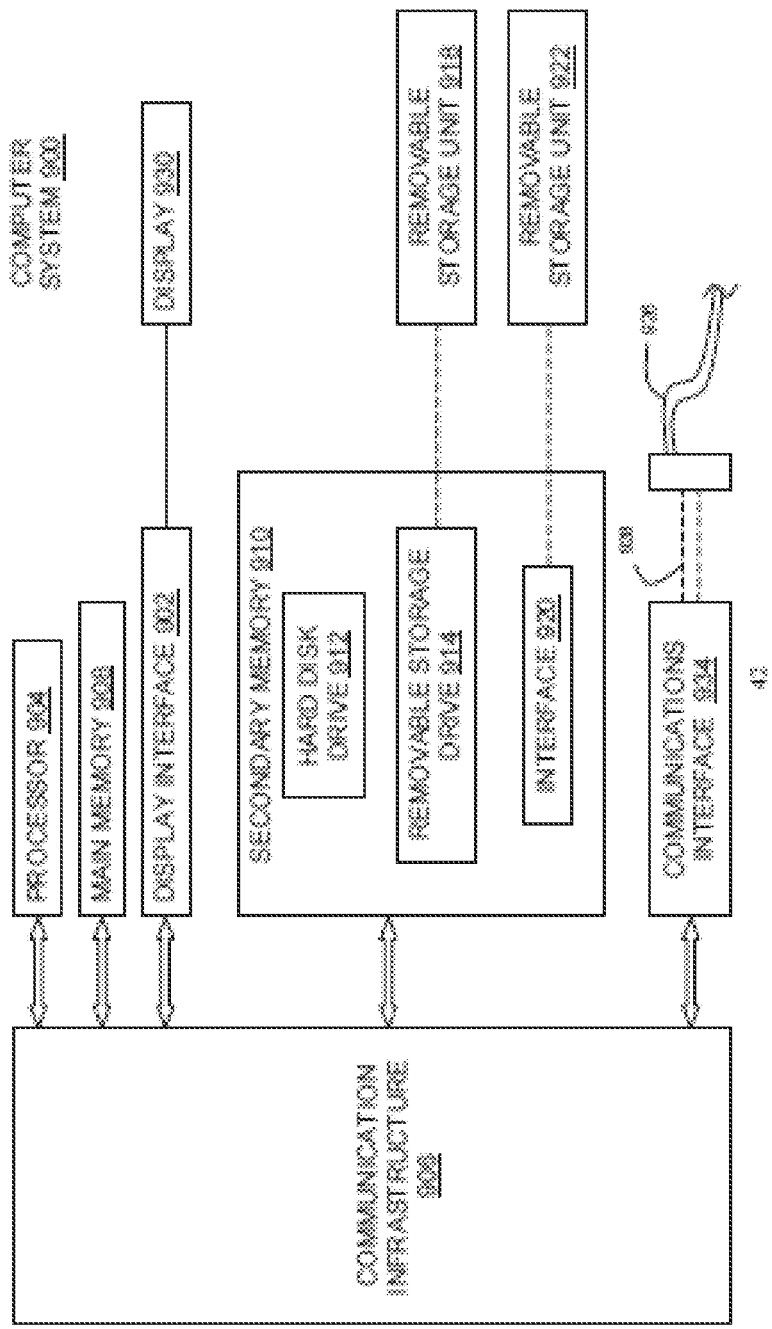
FIG. 11 is a schematic block diagram for a system or related method of an embodiment of the present invention in whole or in part.

Turning to FIG. 11, FIG. 11 is a functional block diagram for a computer system 900 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 90 as illustrated in FIG. 11. The computer system 900 may includes one or more processors, such as processor 904. The Processor 904 is connected to a communication infrastructure 906 (e.g., a communications bus, cross-over bar, or network). The computer system 900 may include a display interface 902 that forwards graphics, text, and/or other data from the communication infrastructure 906 (or from a frame buffer not shown) for display on the display unit 930. For example, information indicating an inferred location of an access needle, warnings related to an inferred location, etc. Display unit 930 may be digital and/or analog.

The computer system 900 may also include a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, a flash memory, etc. The removable storage drive 914 reads from and/or writes to a removable storage unit 918 in a well known manner. Removable storage unit 918, represents a floppy disk, magnetic tape, optical disk, etc. which is read by and written to by removable storage drive 914. As will be appreciated, the removable storage unit 918 includes a computer usable storage medium having stored therein computer software and/or data.

In alternative embodiments, secondary memory 910 may include other means for allowing computer programs or other instructions to be loaded into computer system 900. Such means may include, for example, a removable storage unit 922 and an interface 920. Examples of such removable storage units/interfaces include a program cartridge and cartridge interface (such as that found in video game devices), a removable memory chip (such as a ROM, PROM, EPROM or EEPROM) and associated socket, and other removable storage units 922 and interfaces 920 which allow software and data to be transferred from the removable storage unit 922 to computer system 900.

The computer system 900 may also include a communications interface 924. Communications interface 124 allows software and data to be transferred between computer system 900 and external devices, including, for example, pressure sensors as described herein, ECGs, etc. The communications interface 924 may include a plurality of physical and/or virtual input/output ports configured to communicate with different sensors, etc. Examples of communications interface 924 may include a modem, a network interface (such as an Ethernet card), a communications port (e.g., serial or parallel, etc.), a PCMCIA slot and card, a modem, wifi, Bluetooth, etc. Software and data transferred via communications interface 924 are in the form of signals 928 which may be electronic, electromagnetic, optical or other signals capable of being received by communications interface 924. Signals 928 are provided to communications interface 924 via a communications path (i.e., channel) 926. Channel 926 (or any other communication means or channel disclosed herein) carries signals 928 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 914, a hard disk installed in hard disk drive 912, and signals 928. These computer program products ("computer program medium" and "computer usable medium") are means for providing software to computer system 900. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 908 and/or secondary memory 910. Computer programs may also be received via communications interface 924. Such computer programs, when executed, enable computer system 900 to perform the features of the present invention as discussed herein. In particular, the computer programs, when executed, enable processor 904 to perform the functions of the present invention. Accordingly, such computer programs represent controllers of computer system 900.

In an embodiment where the invention is implemented using software, the software may be stored in a computer program product and loaded into computer system 900 using removable storage drive 914, hard drive 912 or communications interface 924. The control logic (software or computer program logic), when executed by the processor 904, causes the processor 904 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

An aspect of an embodiment may include, but not limited thereto, approaches to visualize tissues via an imaging-equipped epicardial access needle during insertion and passage of it towards the heart, such as the image capture camera being integral to the distal tip of the needle, or outside of the needle with a coherent fiber optic bundle used to convey the optical signal to it from the distal tip.

In some examples, a very small camera may be used, fitting inside the access needle. In examples, the image at the proximal end of the fiber optic bundle may be magnified by a fiber-optic beam expander in order to provide a useful image for detection by the camera. The beam expansion process may or may not require image intensification, e.g. depending on the initial brightness of the target tissues.

A miniature camera may be, for example, fixed inside the distal end of the lumen of the access needle, or it might be integral to an obturator that can be slid into the lumen of the access needle. In either case, a flow channel may be used through which saline or some other liquid can be pumped, e.g. in order to clear debris from the camera aperture.

In some examples, a fiber optic bundle may be fixed inside the lumen of the access needle, or it might be situated inside an obturator that can be slid into the lumen of the access needle. A flow channel for clearing the input aperture of the fiber optic bundle may also be used for this case as well.

Embodiments may include illumination of the target tissues in order to visualize them. This could be done, for example but not limited thereto, by passing a light beam down one or more optical fibers extending along the length of the access needle (either positioned inside it or perhaps arrayed in a fixed configuration on the outside of the shaft). An LED, a laser diode, or some other suitable source of white light may be used to drive the illumination fibers. It may have a separate control for intensity of illumination.

Figure 12:
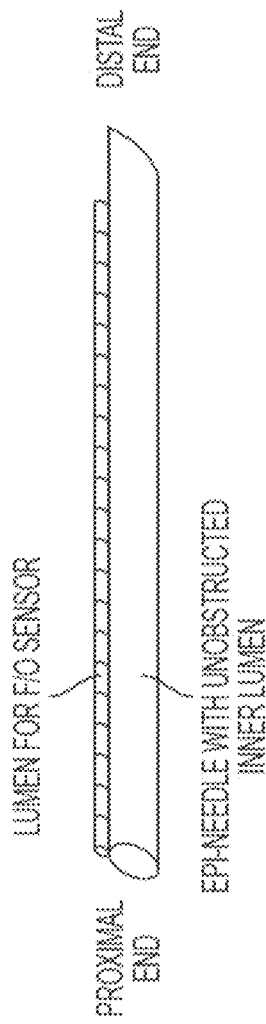
FIG. 12 is an elevation view of an access needle with unobstructed inner lumen according to aspects of the invention.

FIG. 12 is an elevation view of an access needle with unobstructed inner lumen and a second lumen for an F/O sensor or other device, according to aspects of the invention. An imaging fiber bundle may be used either in place of or in addition to the pressure-frequency-sensing optical fiber that is intrinsic to the epicardial access needle. An additional option may include incorporation of a temperature-sensing optical fiber, e.g. in case there is concern about tissue heating associated with any high-intensity optical illumination needed for adequate visualization of the tissues. The F/O lumen may be configured to accommodate and/or include one or more of a pressure sensor, a temperature sensor, a coherent bundle for imaging, or combinations thereof. The access needle may have an open lumen for insertion of a combination of the sensors mentioned above and/or a flush line, and/or a F/O illumination device.

Figure 13:
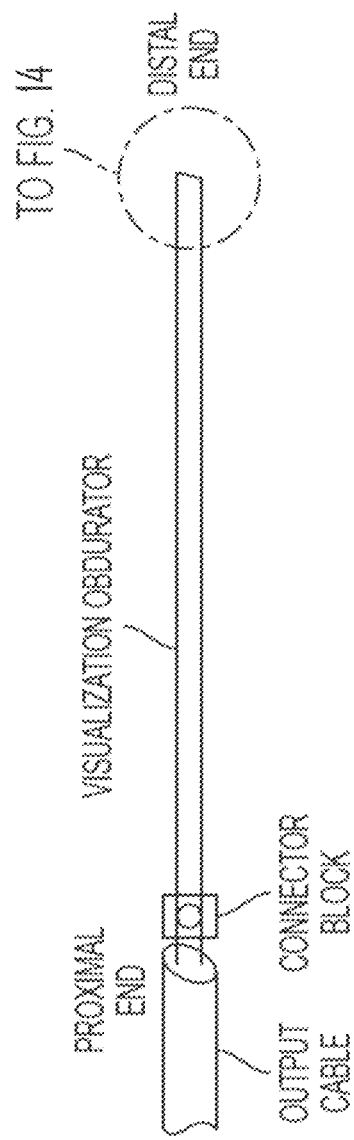
FIG. 13 is an elevation view of visualization obturator according to aspects of the invention.

FIG. 13 is an elevation view of visualization obturator according to aspects of the invention. The visualization obturator includes a proximal end attached to an output cable, a connector block, and a distal end, further details of which are shown in FIG. 14.

Figure 14:
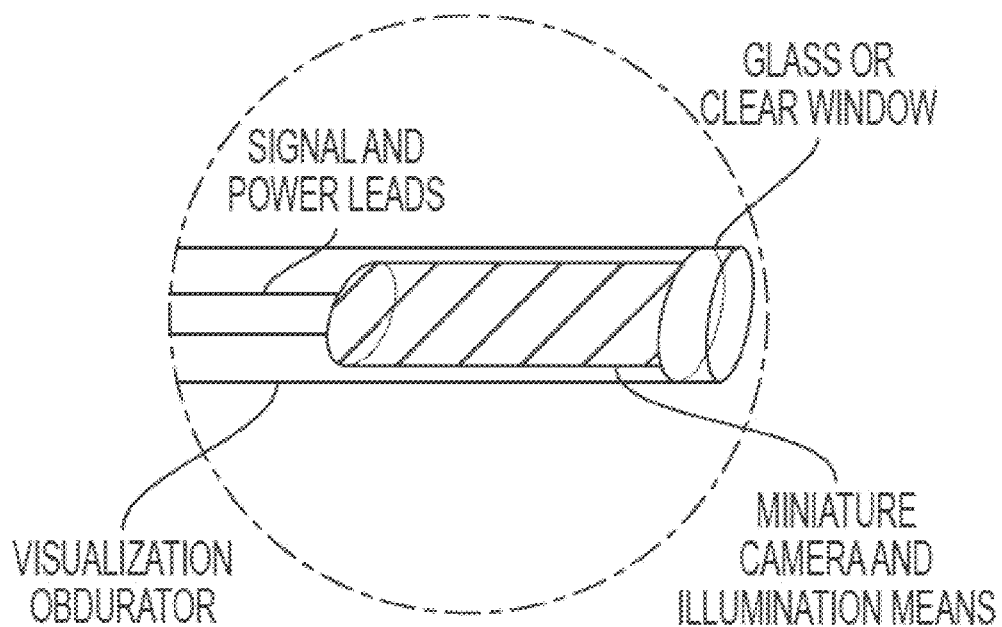
FIG. 14 is an expanded partial view of FIG. 13 at the distal end of visualization obturator including a miniature camera.

FIG. 14 is an expanded partial view of FIG. 13 at the distal end of visualization obturator including a miniature camera. As shown in FIG. 14, the distal end may include a miniature camera attached to signal and power leads, an illumination device, and a glass or other clear window.

Figure 15:
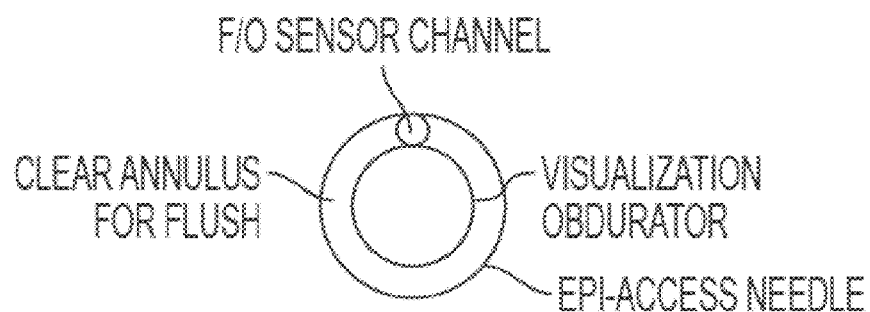
FIG. 15 is an end view of visualization obturator within access needle according to aspects of the invention.

FIG. 15 is an end view of visualization obturator within access needle according to aspects of the invention. As shown in FIG. 15, the access needle may include a middle lumen in which the visualization obturator is slid, a second lumen in which another sensor, illuminator or other device may be accommodated, and/or an annulus that may be used, for example, for flushing and/or suction.

Figure 16:
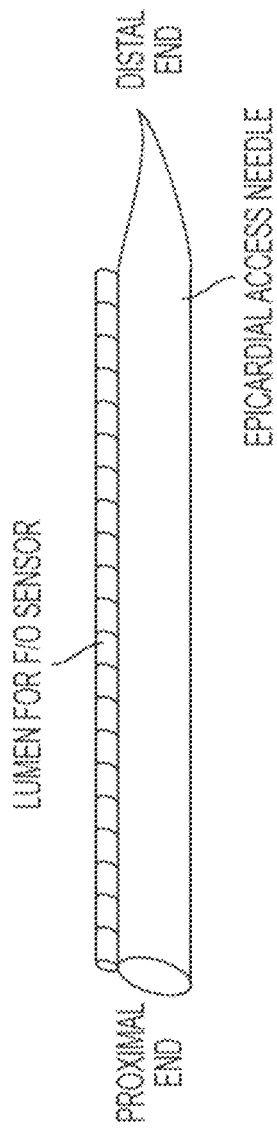
FIG. 16 is an elevation view of an access needle with unobstructed inner lumen according to aspects of the invention.

FIG. 16 is an elevation view of an access needle with unobstructed inner lumen according to aspects of the invention. The F/O lumen may be configured to accommodate and/or include one or more of a pressure sensor, a temperature sensor, a coherent bundle for imaging, or combinations thereof. The access needle may have an open lumen for insertion of a combination of the sensors mentioned above and/or a flush line, and/or a F/O illumination device.

Figure 17:
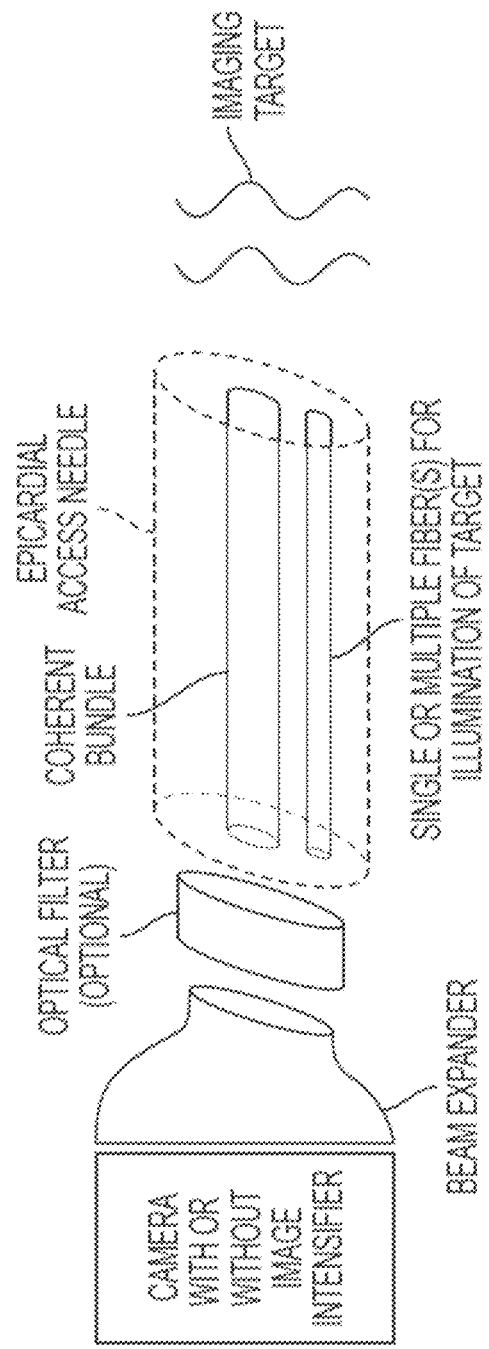
FIG. 17 is a schematic exploded view of imaging elements associated with a fiber optic sensor according to aspects of the invention.

FIG. 17 is a schematic exploded view of imaging elements associated with a fiber optic sensor according to aspects of the invention. As shown in FIG. 17, an optical filter may be provided, e.g. to reduce glare or eliminate reflections. An optical filter may be needed, for example, either in front of the aperture of a distal-tip camera, or either before or after the optical beam expander of the fiber optic bundle in order to minimize the effects of glare (from wet tissues) and multiple reflections. This may also be accomplished, for example, by suitable coatings on the camera and/or fiber optic bundle distal apertures. A camera (with or without image intensifier) may be coupled to the beam expender and/or optical filter, and linked to the coherent bundle and/or illumination fiber(s) running through the access needle.

Figure 18:
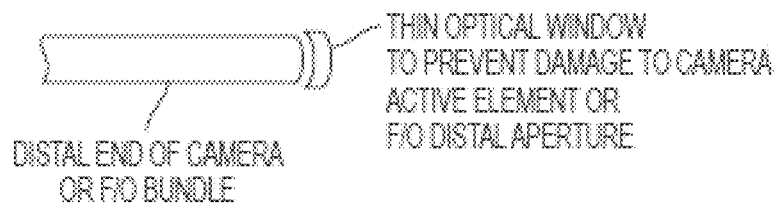
FIG. 18 is a schematic diagram of a distal end of a camera having a thin optical window according to aspects of the invention.

FIG. 18 is a schematic diagram of a distal end of a camera or F/O bundle having a thin optical window according to aspects of the invention. The optical window may be provided, for examples, to prevent damage to a camera active element.

Figure 19:
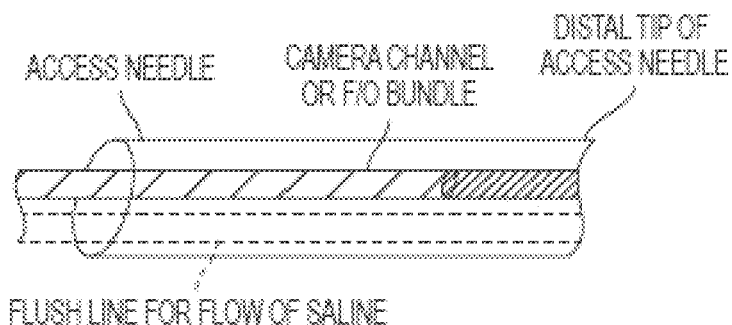
FIG. 19 is an elevation view of the distal tip of an access needle including a flush line according to aspects of the invention.

FIG. 19 is an elevation view of the distal tip of an access needle including a flush line according to aspects of the invention. The flush line that may be used, for examples, for clearing debris from blocking field-of-view at distal tip.

Figure 20:
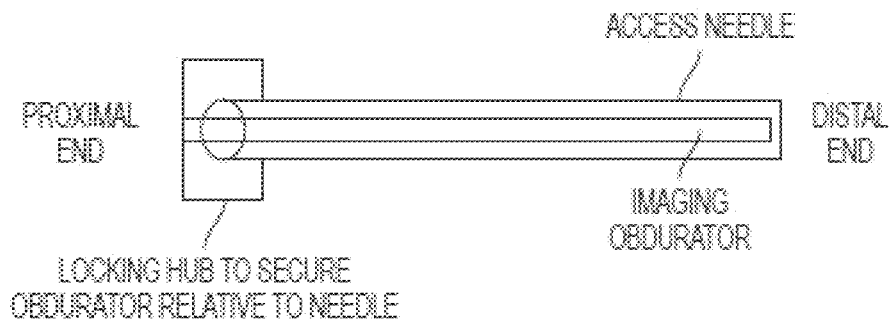
FIG. 20 is an elevation view of access needle and visualization obturator with a locking mechanism according to aspects of the invention.

FIG. 20 is an elevation view of access needle and visualization obturator with a locking mechanism according to aspects of the invention. In some examples, if an obturator approach is used, there may be a locking mechanism at the proximal hub to secure the obturator in a fixed axial and angular position it inside the access needle.

Figure 21:
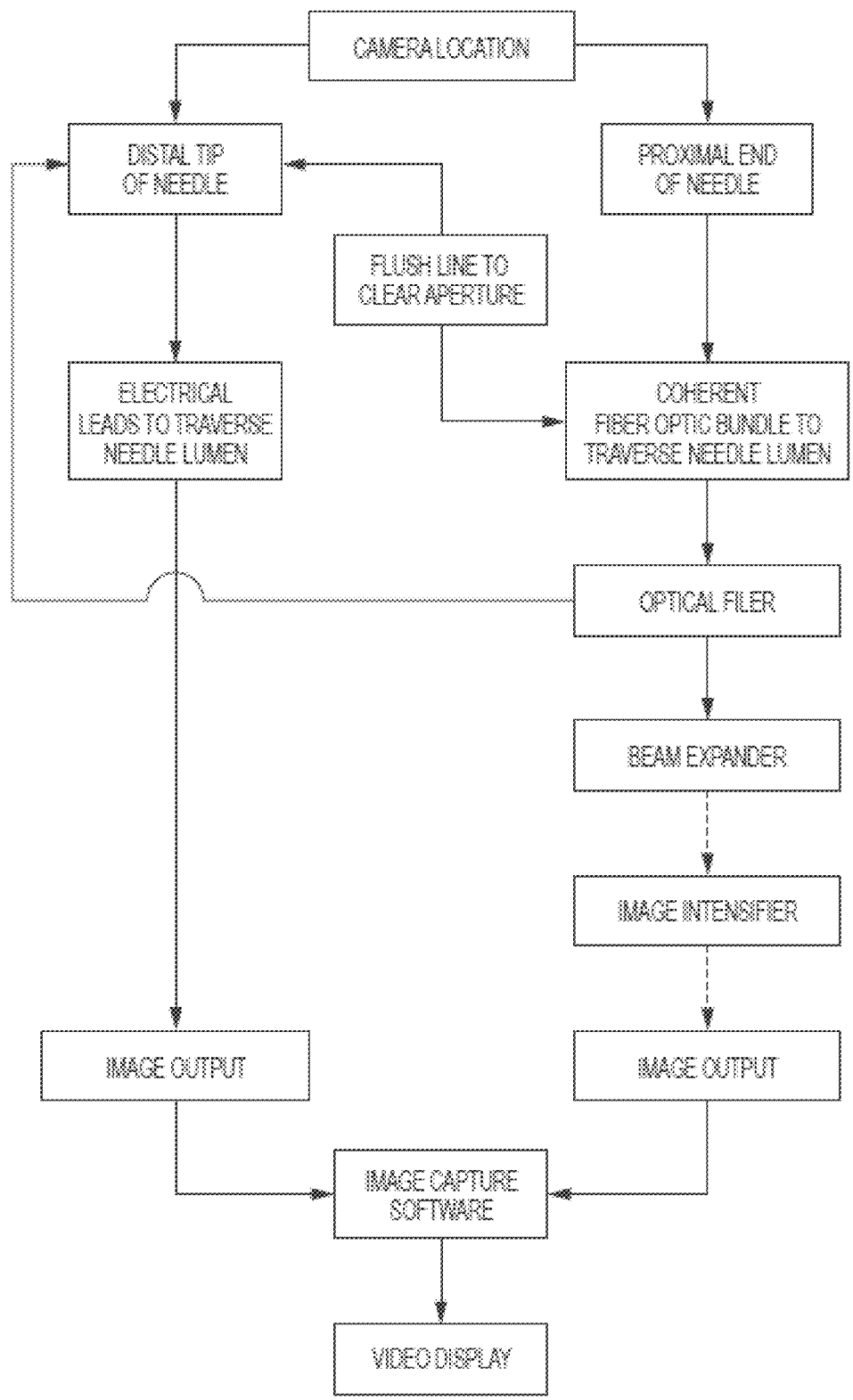
FIG. 21 is a flow chart for a direct visualization technique according to aspects of the invention.

FIG. 21 is a relational diagram for a direct visualization technique according to aspects of the invention. It is also noted that, flowcharts for realizing imaging chains described herein, may typically require that the output signal be acquired by image capture software. The resulting views of the tissues in front of the needle can then be either displayed on a video screen, archived for use later, or both.

Figure 22:
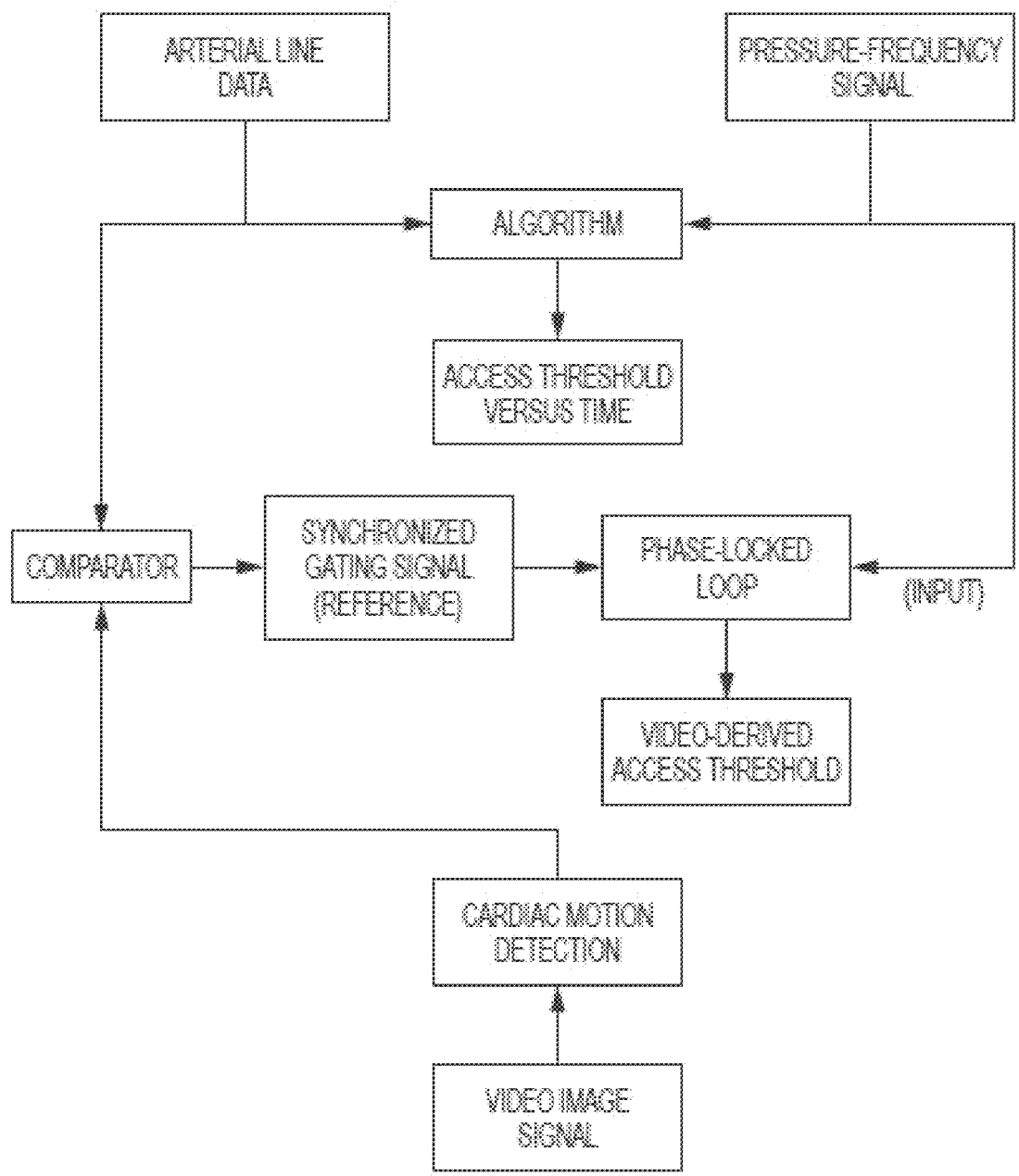
FIG. 22 is a flow chart for synchronization of direct visualization and pressure-frequency information according to aspects of the invention.

Direct visualization can be a useful adjunct to pressure-frequency sensing during needle navigation. In and of itself, in some instances, it may not provide quantitative information about the cardio-dynamic environment at the needle's tip, but the images might be synchronized to the pressure-frequency algorithm's output to provide a deeper and more intuitive understanding of it. FIG. 22 is a flow chart including aspects related to synchronization of direct visualization and pressure-frequency information.

The present inventor has investigated the use of direct visualization to enhance minimally invasive epicardial procedures. In an approach, a miniature camera was placed in a prototype subxiphoid introducer needle, and bench top, in vitro and in vivo tests of system performance were made during simulated and actual attempts at pericardial access and cardio-endoscopy. This system had an unshielded field of view of 100° and a resolution of 220×224 pixels. When a sleeve used to maintain depth of field was slid past the distal tip of the camera probe, the field of view would decrease by ≈15° per millimeter of sleeve extension, but without loss of image quality. While tests during in vivo subxiphoid access in a porcine model revealed that the pericardial membrane may have been more difficult to localize, the results also showed excellent resolution of the coronary arteries on the epicardial surface.

Figure 23A:
FIGS. 23A and 23B show two characteristic images captured during the advance of the needle towards the pericardium.
Figure 23B:
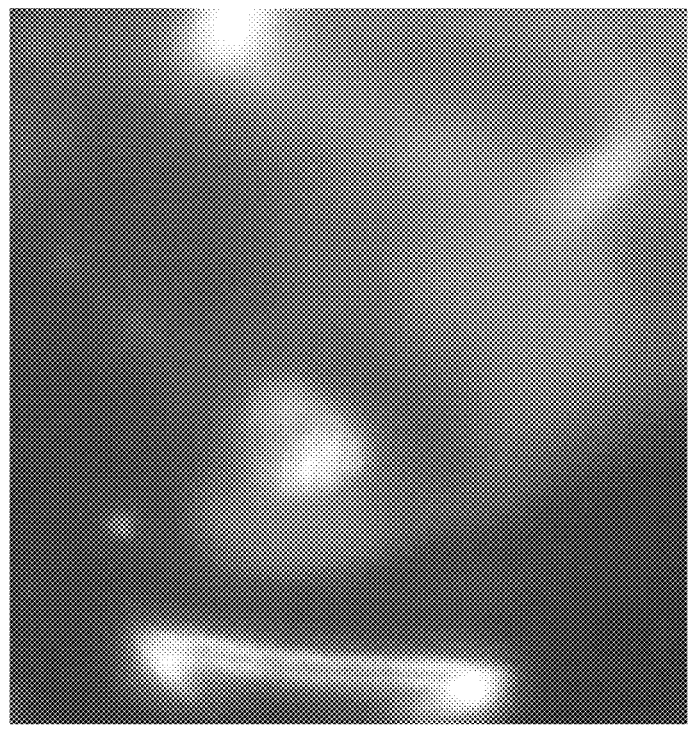

Using an introducer needle as described above, with the windowed-camera probe internal to it, subxiphoid puncture was carried out and the needle advanced toward the heart. The live video feed from the camera was displayed continuously on the imaging system's HD monitor during the access procedure. FIGS. 23A and 23B show two characteristic images captured during the advance of the needle towards the pericardium. FIG. 23A is the forward-looking view as seen from an intermediate point within the chest, showing the rather indistinct surface of the pericardium in the upper half of the image. FIG. 23B is the image seen when the introducer has reached the pericardium. As expected, the smooth, moist surface of the pericardial membrane is partially optically reflective as indicated by the glare zones produced by the probe's illumination. This, and its translucency, can make it difficult to identify either the surface morphology of the pericardium or any anatomical features of the epicardial wall beneath it. Another factor affecting image quality may also be residual fogging of the window on the distal tip of the camera-sleeve assembly, due smearing by adjacent tissues and/or contact with other effluent materials.

The miniature camera tested in this work provided very useful high resolution images over a large linear depth of field and angular field of view. The present inventor was able to incorporate it straightforwardly as a component of a prototype imaging system that in principle would be largely compatible with the mechanical structure and clinical function of either the EpiAccess™ needle (See U.S. patent application Ser. No. 13/607,993 entitled "Access Needle Pressure Sensor Device and Method of Use," filed Sep. 10, 2012; U.S. Patent Application Publication No. US-2012-0330184, Dec. 27, 2012; U.S. patent application Ser. No. 12/530,830 entitled "Access Needle Pressure Sensor Device and Method of Use," filed Sep. 11, 2009, now U.S. Pat. No. 8,282,565, issued Oct. 9, 2012; of which are hereby incorporated by reference herein in their entirety) or a stand-alone cardio-endoscope.

The description given above is merely illustrative and is not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the memory circuit design, memory circuit manufacture or related fields are intended to be within the scope of the appended claims.

The following patents, applications and publications as listed below and throughout this document (which are not admitted to be prior art with respect to the present invention by inclusion in this section) are hereby incorporated by reference in their entirety herein:

1. U.S. patent application Ser. No. 13/885,157 entitled "Remotely Controlled and/or Laterally Supported Devices for Direct Spinal Cord Stimulation," filed May 13, 2013.
2. International Patent Application No. PCT/US2011/060462 entitled "Remotely Controlled and/or Laterally Supported Devices for Direct Spinal Cord Stimulation," filed Nov. 11, 2011.
3. U.S. patent application Ser. No. 13/780,207 entitled "System and Method for Magnetic Control of an Anesthetic," filed Feb. 28, 2013; U.S. Patent Application Publication No. 2013/0225904, Aug. 29, 2013.
4. U.S. patent application Ser. No. 13/704,782 entitled "METERS FOR IN-VIVO MONITORING," filed Jul. 30, 2013.
5. International Patent Application No. PCT/US2011/040976 entitled "METERS FOR IN-VIVO MONITORING," filed Jun. 17, 2011.
6. U.S. patent application Ser. No. 13/780,207 entitled "System and Method for Magnetic Control of an Anesthetic," filed Feb. 28, 2013.
7. U.S. patent application Ser. No. 13/607,993 entitled "Access Needle Pressure Sensor Device and Method of Use," filed Sep. 10, 2012; U.S. Patent Application Publication No. US-2012-0330184, Dec. 27, 2012.
8. U.S. patent application Ser. No. 12/530,830 entitled "Access Needle Pressure Sensor Device and Method of Use," filed Sep. 11, 2009.
9. International Patent Application No. PCT/US2008/056643 entitled "Access Needle Pressure Sensor Device and Method of Use," filed Mar. 12, 2008.
10. U.S. patent application Ser. No. 13/579,745 entitled "ACCESS SYSTEM FOR FEMORAL VASCULATURE CATHETERIZATION AND RELATED METHOD," filed Aug. 17, 2012.
11. International Patent Application No. PCT/US2010/061413 entitled "ACCESS SYSTEM FOR FEMORAL VASCULATURE CATHETERIZATION AND RELATED METHOD," filed Dec. 21, 2010.
12. U.S. patent application Ser. No. 13/579,882 entitled "SYSTEM, METHOD, AND COMPUTER PROGRAM PRODUCT FOR SIMULATING EPICARDIAL ELECTROPHYSIOLOGY PROCEDURES," filed Aug. 17, 2012.
13. International Patent Application No. PCT/US2011/025470 entitled "SYSTEM, METHOD, AND COMPUTER PROGRAM PRODUCT FOR SIMULATING EPICARDIAL ELECTROPHYSIOLOGY PROCEDURES," filed Feb. 18, 2011; U.S. Patent Application Publication No. WO 2011/103456, Aug. 25, 2011.
14. U.S. patent application Ser. No. 13/559,008 entitled "Blood Flow Bypass Catheters and Methods for the Delivery of Medium to the Vasculature and Body Ducts," filed Jul. 26, 2012.
15. U.S. patent application Ser. No. 12/625,153 entitled "Blood Flow Bypass Catheters and Methods for the Delivery of Medium to the Vasculature and Body Ducts," filed Nov. 24, 2009; U.S. Pat. No. 8,255,193, issued Aug. 28, 2012.
16. U.S. patent application Ser. No. 11/884,421 entitled "Blood Flow Bypass Catheters and Methods for the Delivery of Medium to the Vasculature and Body Ducts," filed Aug. 15, 2007.
17. International Patent Application No. US2006/005876 entitled "Blood Flow Bypass Catheters and Methods for the Delivery of Medium to the Vasculature and Body Ducts," filed Feb. 16, 2006.
18. U.S. patent application Ser. No. 13/540,348 entitled "Coaxial Catheter Systems for Transference of Medium," filed Jul. 2, 2012; U.S. Patent Application Publication No. 2013/0090556, Apr. 11, 2013.
19. U.S. patent application Ser. No. 12/760,837 entitled "Coaxial Catheter Systems for Transference of Medium," filed Apr. 15, 2010; U.S. Pat. No. 8,211,083, issued Jul. 3, 2012.
20. U.S. patent application Ser. No. 11/191,676 entitled "Coaxial Catheter Systems for Transference of Medium," filed Jul. 28, 2005; U.S. Pat. No. 7,727,225, issued Jun. 1, 2010.
21. International Patent Application No. PCT/US2005/026738 entitled "Coaxial Catheter Systems for Transference of Medium," filed Jul. 28, 2005.
22. U.S. patent application Ser. No. 13/464,762 entitled "SYSTEMS AND METHODS FOR DETERMINING LOCATION OF AN ACCESS NEEDLE IN A SUBJECT," filed May 4, 2012; U.S. Patent Application Publication No. US-2012-0283582-A1, Nov. 8, 2012.
23. U.S. patent application Ser. No. 13/464,752 entitled "SYSTEMS AND METHODS FOR DETERMINING LOCATION OF AN ACCESS NEEDLE IN A SUBJECT," filed May 4, 2012; U.S. Patent Application Publication No. US-2012-0310052-A1, Dec. 6, 2012.
24. U.S. patent application Ser. No. 13/318,450 entitled "ACCESS TROCAR AND RELATED METHOD THEREOF," filed Nov. 1, 2011, now U.S. Pat. No. 8,906,056, issued Dec. 9, 2014.
25. International Patent Application No. PCT/US2010/033189 entitled "ACCESS TROCAR AND RELATED METHOD THEREOF," filed Apr. 30, 2010.
26. U.S. patent application Ser. No. 12/741,710 entitled "STEERABLE EPICARDIAL PACING CATHETER SYSTEM PLACED VIA THE SUBXIPHOID PROCESS," filed May 6, 2010; U.S. Patent Application Publication No. 2010/0241185, Sep. 23, 2010.
27. International Patent Application No. PCT/US2008/082835 entitled "STEERABLE EPICARDIAL PACING CATHETER SYSTEM PLACED VIA THE SUBXIPHOID PROCESS," filed Nov. 7, 2008.
28. U.S. patent application Ser. No. 12/513,258 entitled "Means and Methods for Cytometric Therapies," filed Mar. 17, 2010; U.S. Patent Application Publication No. 2010/0210927, Aug. 19, 2010.
29. International Patent Application No. PCT/US2007/023047 entitled "Means and Methods for Cytometric Therapies," filed Nov. 1, 2007.

30. International Patent Application No. US2006/005876 entitled "Blood Flow Bypass Catheters and Methods for the Delivery of Medium to the Vasculature and Body Ducts," filed Feb. 16, 2006.
31. U.S. patent application Ser. No. 12/532,233 entitled "Electrode Catheter for Ablation Purposes and Related Method Thereof," filed Sep. 21, 2009; U.S. Patent Application Publication No. 2010/0211064, Aug. 19, 2010.
32. International Patent Application No. PCT/US2008/057626 entitled "Electrode Catheter for Ablation Purposes and Related Method Thereof," filed Mar. 20, 2008.
33. U.S. patent application Ser. No. 12/530,938 entitled "Epicardial Ablation Catheter and Method of Use," filed Sep. 11, 2009; U.S. Patent Application Publication No. 2010/0114093, May 6, 2010.
34. International Patent Application No. PCT/US2008/056816 entitled "Epicardial Ablation Catheter and Method of Use," filed Mar. 13, 2008.
35. U.S. patent application Ser. No. 12/304,801 entitled "Closure Device for Skull Plates and Related Method Thereof," filed May 18, 2009; U.S. Pat. No. 8,226,694, issued Jul. 24, 2012.
36. International Patent Application No. PCT/US2007/014881 entitled "Closure Device for Skull Plates and Related Method Thereof," filed Jun. 26, 2007.
37. U.S. patent application Ser. No. 12/375,139 entitled "System and Method for Intracranial Implantation of Therapeutic or Diagnostic Agents," filed Jan. 27, 2009; U.S. Patent Application Publication No. 2009/0192487, Jul. 30, 2009.
38. International Patent Application No. PCT/US2007/016256 entitled "System and Method for Intracranial Implantation of Therapeutic or Diagnostic Agents," filed Jul. 18, 2007.
39. U.S. patent application Ser. No. 12/160,378 entitled "Multi-Port Catheter System with Medium Control and Measurement Systems for Therapy and Diagnosis Delivery," filed Aug. 1, 2008; U.S. Patent Application Publication No. 2009-0048577, Feb. 19, 2009.
40. International Patent Application No. PCT/US2007/000353 entitled "Multi-Port Catheter System with Medium Control and Measurement Systems for Therapy and Diagnosis Delivery," filed Jan. 9, 2007.
41. International Patent Application No. US2006/013621 entitled "Catheter Systems for Delivery of Agents and Related Method Thereof," filed Apr. 12, 2006.
42. U.S. patent application Ser. No. 11/105,166 entitled "Catheter Systems for Delivery of Agents and Related Method Thereof," filed Apr. 13, 2005; U.S. Pat. No. 7,670,327, issued Mar. 2, 2010.
43. U.S. patent application Ser. No. 10/985,340 entitled "Catheter Navigation Within an MR Imaging Device," filed Nov. 10, 2004.
44. U.S. patent application Ser. No. 10/429,524 entitled "Catheter Navigation Within an MR Imaging Device," filed May 5, 2003; U.S. Pat. No. 6,834,201, issued Dec. 21, 2004.
45. International Patent Application No. US02/02363 entitled "Catheter Navigation within an MR Imaging Device," filed Jan. 28, 2002.
46. U.S. patent application Ser. No. 09/772,188 entitled "Catheter Navigation within an MR Imaging Device," filed Jan. 29, 2001.
47. U.S. patent application Ser. No. 10/444,884 entitled "Cell Delivery Catheter and Method," filed May 23, 2003; U.S. Pat. No. 8,096,984, issued Jan. 17, 2012.
48. U.S. patent application Ser. No. 09/574,857 entitled "Cell Delivery Catheter and Method," filed May 19, 2000; U.S. Pat. No. 6,599,274, issued Jul. 29, 2003.
49. U.S. patent application Ser. No. 09/859,472 entitled "Continuous Metal Fiber Brushes," filed May 18, 2001.
50. U.S. patent application Ser. No. 09/147,100 entitled "Continuous Metal Fiber Brushes," filed Apr. 4, 1997; U.S. Pat. No. 6,245,440, issued Jun. 12, 2001.
51. International Patent Application No. US97/05149 entitled "CONTINUOUS METAL FIBER BRUSHES," filed Apr. 4, 1997.
52. U.S. patent application Ser. No. 09/548,110 entitled "Multi-Probe System," filed Apr. 12, 2000; U.S. Pat. No. 6,626,902, issued Sep. 30, 2003.
53. International Patent Application No. US99/24253 entitled "MRI AND MAGNETIC STEREOTAXIS SURGICAL SYSTEM," filed Oct. 15, 1999.
54. U.S. patent application Ser. No. 09/174,189 entitled "Combined Magnetic Resonance Imaging and Magnetic Stereotaxis Surgical Apparatus and Processes," filed Oct. 16, 1998; U.S. Pat. No. 6,298,259, issued Oct. 2, 2001.
55. International Patent Application No. US99/17880 entitled "MR-Visible Device for Magnetic Stereotaxis Neurological Interventions," filed Aug. 6, 1999.
56. U.S. patent application Ser. No. 09/131,031 entitled "MR-Visible Medical Device for Neurological Interventions Using Nonlinear Magnetic Stereotaxis and a Method Imaging," filed Aug. 7, 1998;
57. U.S. Pat. No. 6,272,370, issued Aug. 7, 2001.
58. U.S. patent application Ser. No. 09/114,414 entitled "Magnetic Stereotactic System for Treatment Delivery," filed Jul. 13, 1998.
59. U.S. patent application Ser. No. 08/464,279 entitled "Magnetic Stereotactic System for Treatment Delivery," filed Jun. 5, 1995; U.S. Pat. No. 5,707,335, issued Jan. 13, 1998.
60. U.S. patent application Ser. No. 08/096,214 entitled "Magnetic Stereotactic System for Treatment Delivery," filed Jul. 19, 1993; U.S. Pat. No. 5,779,694, issued Jul. 14, 1998.
61. U.S. patent application Ser. No. 07/904,032 entitled "MAGNETIC STEREOTACTIC SYSTEM FOR TREATMENT DELIVERY," filed Jun. 25, 1992.
62. U.S. patent application Ser. No. 07/463,340 entitled "Magnetic Stereotactic System for Treatment Delivery," filed Jan. 10, 1990.

REFERENCES CITED

The following patents, applications and publications as listed below and throughout this document are hereby incorporated by reference in their entirety herein.

Foreign Patent Documents

WO95/10319, Fleischman, et al., "Electrodes for Creating Lesions in Body Tissue", April 1995.
EP 1 129 681 A1, Pezzola, A., "Phacoemulsification Tip", September 2001.

Other Publications

J. Tucker-Schwartz et al., "Improved Pressure-Frequency Sensing Subxiphoid Pericardial Access System: Performance Characteristics During In Vivo testing," IEEE Transactions on Biomedical Engineering, Vol. 58, pp. 845-852 (April 2011).

J. Tucker-Schwartz et al., "Pressure-Frequency Sensing Subxiphoid Access System for Use in Percutaneous Cardiac Electrophysiology: Prototype Design and Pilot Study Results," IEEE Transactions on Biomedical Engineering, Vol. 56, pp. 1160-1168 (May 2009).

F. Sacher, P. Maury, I. Nault, M. Wright, N. Lellouche, N. Derval, S. Ploux, M. Hocini, P. Bordachar, A. Deplagne, P. Ritter, J. Clementy, M. Haissaguerre, and P. Jais, "Prevalence of epicardial scar in patients referred for ventricular tachycardia ablation," *Heart Rhythm*, vol. 6, pp. S175-6, 2009.

C. Grimard, J. Lacotte, F. Hidden-Lucet, G. Duthoit, Y. Gallais, and R. Frank, "Percutaneous epicardial radiofrequency ablation of ventricular arrhythmias after failure of endocardial epproach: a 9-year experience," *J. Cardiovasc. Electrophysiol.*, vol. 21, no. 1, pp. 56-61, 2010.

E. Aliot, W. Stevenson, J. Almendral-Garrote, F. Bogun, C. Calkins, E. Delacretaz, P. Bella, G. Hindricks, P. Jais, M. Josephson, J. Kautzner, G. Kay, K. Kuck, B. Lerman, F. Marchlinski, V. Reddy, M. Schalij, R. Schilling, L. Soejima, and D. Wilber, "EHRA/HRS expert consensus on catheter albation of ventricular arrhythmias," *Europace*, vol. 11, no. 6, pp. 771-817, 2009.

E. Sosa, M. Scanavacca, A. d'Avila, and F. Pilleggi, "A new technique to perform epicardial mapping in the electrophysiology laboratory," *J. Cardiovasc. Electrophysiol.*, vol. 7, no. 6, pp. 531-6, 1996.

E. Sosa, M. Scanavacca, A. d'Avila, J. Piccioni, O. Sanchez, J. Velarde, M. Silva, and B. Reolao, "Endocardial and epicardial ablation guided by nonsurgical transthoracic epicardial mapping to treat recurrent ventricular tachycardia," *J. Cardiovasc. Electrophysiol.*, vol. 9, no. 3, pp. 229-39, 1998.

E. Sosa, M. Scanavacca, A. d'Avila, F. Oliviera, and J. Ramires, "Nonsurgical transthoracic epicardial catheter ablation to treat recurrent ventricular tachycardia occurring late after myocardial infarction," *J. Am. Coll. Cardiol.*, vol. 35, no. 6, pp. 1442-9, 2000.

E. Sosa and M. Scanavacca, "Epicardial mapping and ablation techniques to control ventricular tachycardia," *J. Cardiovasc. Electrophysiol.*, vol. 16, no. 4, pp. 449-52, 2005.

U. Tedrow and W. Stevenson, "Strategies for epicardial mapping and ablation of ventricular tachycardia," *J. Cardiovasc. Electrophysiol.*, vol. 20, no. 6, pp. 710-3, 2009.

S. Mahapatra, J. Tucker-Schwartz, D. Wiggins, G. Gillies, P. Mason, G. McDaniel, D. Lapar, C. Stemland, E. Sosa, J. Ferguson, T. Bunch, G. Ailawadi, and M. Scanavacca, "Pressure frequency characteristics of the pericardial space and thorax during subxiphoid access for epicardial ventricular tachycardia ablation," *Heart Rhythm*, vol. 7, no. 5, pp. 604-9, 2010.

The disclosures of all references and publications cited above are expressly incorporated by reference in their entireties to the same extent as if each were incorporated by reference individually.

What is claimed is:

1. A system for accessing one or more locations of a subject, said system comprising:
    an access needle having a first lumen, a second lumen, a distal end and a proximal end;
    a first sensor configured for sensing pressure frequency in the one or more locations of the subject, and accommodated in at least one of the first or second lumens;
    an imaging device including a camera configured for obtaining image data in the one or more locations of the subject, and accommodated in at least one of the first or second lumens;
    an illumination device configured for illuminating the one or more locations of the subject, and accommodated in at least one of the first or second lumens; and
    a cleaner configured to cleanse an aperture of the camera of the imaging device while in the one or more locations of the subject.

2. The system of claim 1, further comprising a computer processor configured to determine a location of the access needle based at least in part on sensed pressure frequency information, wherein the processor is further configured to:
    receive pressure frequency information for the subject from the first sensor;
    receive cardiac waveform information for the subject;
    determine a reference phase based on the cardiac waveform information; and
    determine a test phase based on the pressure frequency information,
    wherein, determining the location of the access needle is based on the pressure frequency information from the test phase and the cardiac waveform information from the reference phase.

3. The system of claim 2, wherein said determining the location of the access needle includes comparing the algorithm results of the pressure frequency information and the cardiac waveform information to a plurality of predetermined threshold values.

4. The system of claim 2, wherein the pressure frequency information and the cardiac waveform information are combined at least in part by phase sensitive detection and matched filtering.

5. The system of claim 2, wherein the pressure frequency information and the cardiac waveform information are combined at least in part by integrating the pressure frequency information.

6. The system of claim 2, wherein the reference phase is a cardiac phase of the subject immediately preceding the test phase.

7. The system of claim 2, wherein the cardiac waveform information includes information derived from a plurality of cardiac phases of the subject.

8. The system of claim 2, wherein the cardiac waveform information includes at least one of ventricle pressure, arterial pressure, and electrocardiogram (ECG) voltages.

9. The system of claim 1, further comprising at least one of a beam expander or an optical filter coupled to the camera of the imaging device.

10. The system of claim 1, further comprising a second sensor configured for sensing temperature in the one or more locations of the subject while illuminating the one or more locations of the subject, and accommodated in at least one of the first or second lumens.

11. The system of claim 1, wherein the cleaner includes a flush line configured to at least one of provide fluid to the distal end of the access needle or remove fluid from the distal end of the access needle.

12. The system of claim 11, wherein the flush line substantially surrounds the at least one of the first or second lumens in which the camera of the imaging device is accommodated.

13. A system for accessing one or more locations of a subject, said system comprising:
    an access needle having a first lumen, a second lumen, a distal end and a proximal end;

a first sensor configured for sensing pressure frequency in the one or more locations of the subject, and accommodated in at least one of the first or second lumens;

an imaging device configured for obtaining image data in the one or more locations of the subject, and accommodated in at least one of the first or second lumens; and an illumination device configured for illuminating the one or more locations of the subject, wherein, the imaging device includes at least one of a miniature camera configured to slide within at least one of the first or second lumens, or a camera coupled to a fiber optic cable accommodated in at least one of the first or second lumens.

14. The system of claim 13, wherein the imaging device includes the miniature camera configured to slide within at least one of the first or second lumens, wherein the miniature camera is housed in a visual obturator and coupled to an illumination source.

15. The system of claim 13, wherein the imaging device includes the camera coupled to the fiber optic cable accommodated in at least one of the first or second lumens via a coupling, wherein the coupling includes a beam expander and an optical filter between the camera and the fiber optic cable.

16. The system of claim 13, further comprising a processor configured to determine a location of the access needle based at least in part on pressure frequency information.

17. The system of claim 16, wherein determining the location of the access needle is based at least in part on comparing the pressure frequency information to a plurality of predetermined threshold values.

18. The system of claim 13, further comprising a flush line configured to cleanse an aperture of the camera of the imaging device while in the one or more locations of the subject via at least one of providing fluid to the distal end of the access needle or removing fluid from the distal end of the access needle.

19. The system of claim 13, further comprising a second sensor configured for sensing temperature in the one or more locations of the subject while illuminating the one or more locations of the subject.

20. A method of inferring the location of an access needle in a subject, the method comprising:

inserting the access needle into a body of a subject, the access needle having a first lumen, a second lumen, a distal end, a proximal end, a first sensor configured for sensing pressure frequency from the location of the access needle in the subject and accommodated in at least one of the first or second lumens, an imaging device including a camera configured for obtaining image data from the location of the access needle in the subject and accommodated in at least one of the first or second lumens, and an illumination device configured for illuminating the location of the access needle in the subject and accommodated in at least one of the first or second lumens;

receiving image data of the subject from the camera of the imaging device;

receiving pressure frequency information from the first sensor; and determining, by a computer processor, an estimated location of the access needle based on an algorithm including the pressure frequency information while presenting the image data on a display.

21. The method of claim 20, further comprising:

receiving, by the computer processor, cardiac waveform information of the subject;

wherein determining the estimated location of the access needle is based on the pressure frequency information and the cardiac waveform information.

22. The method of claim 21, wherein determining the estimated location of the access needle includes comparing algorithm results of the pressure frequency information and the cardiac waveform information to a plurality of predetermined threshold values.

23. The method of claim 21, wherein the cardiac waveform information includes information derived from a plurality of cardiac phases of the subject.

24. The method of claim 21, wherein the cardiac waveform information includes at least one of ventricle pressure, arterial pressure, and electrocardiogram (ECG) signals.

25. The method of claim 20, wherein the method includes distinguishing between a location remote from the pericardium, a location close to or in contact with the pericardium, and a location inside the pericardium.

26. The method of claim 20, further comprising cleansing an aperture of the camera of the imaging device while the access needle is disposed in the subject via at least one of providing fluid to the distal end of the access needle or removing fluid from the distal end of the access needle.

* * * * *